US007842477B2

(12) United States Patent
Fenge et al.

(10) Patent No.: US 7,842,477 B2
(45) Date of Patent: Nov. 30, 2010

(54) METHODS FOR PRODUCING GAMMA-CARBOXYLATED PROTEINS

(75) Inventors: Christel Fenge, Södertälje (SE); Ann Lövgren, Mölndal (SE); Anders Thelin, Mölndal (SE)

(73) Assignee: AstraZeneca AB, Södertälje (SE)

( * ) Notice: Subject to any disclaimer, the term of this patent is extended or adjusted under 35 U.S.C. 154(b) by 626 days.

(21) Appl. No.: 10/964,888

(22) Filed: Oct. 14, 2004

(65) Prior Publication Data

US 2005/0164367 A1 Jul. 28, 2005

(30) Foreign Application Priority Data

Oct. 14, 2003 (GB) ................................ 0324044.7

(51) Int. Cl.
*C12P 21/02* (2006.01)

(52) U.S. Cl. .......................... 435/69.1; 514/8; 536/24.1

(58) Field of Classification Search ....................... None
See application file for complete search history.

(56) References Cited

U.S. PATENT DOCUMENTS 4,404,187 A 9/1983 Schwinn et al.
4,599,308 A * 7/1986 Hamer et al. .............. 435/69.4
4,784,950 A * 11/1988 Hagen et al. ............... 435/69.6
5,118,614 A 6/1992 Rybák et al.
5,122,458 A 6/1992 Post et al.
5,648,254 A * 7/1997 Mulvihill et al. ............ 435/217
5,866,122 A 2/1999 Turecek et al.
5,958,893 A * 9/1999 Welsh et al. .................. 514/44
5,965,789 A 10/1999 Lubon et al.
6,039,945 A 3/2000 Turecek et al.
6,165,974 A 12/2000 Turecek et al.
6,224,862 B1 5/2001 Turecek et al.
6,224,864 B1 5/2001 Argoudelis et al.
6,342,372 B1 1/2002 Dubensky, Jr. et al.
6,413,737 B1 7/2002 Olsen et al.
7,482,141 B2 1/2009 Stafford et al.
2002/0106381 A1* 8/2002 High ....................... 424/233.1
2004/0197858 A1 10/2004 Yonemura et al.
2005/0164367 A1 7/2005 Fenge et al.
2008/0045453 A1 2/2008 Drohan et al.
2008/0312127 A1 12/2008 Lovgren
2009/0047273 A1 2/2009 Harrysson et al.

FOREIGN PATENT DOCUMENTS

EP 0052827 6/1982
EP 0607392 7/1994
EP 0700682 3/1996
EP 1 407 780 A1 4/2004
EP 1405910 4/2004
EP 1405912 4/2004
EP 1676911 7/2006
WO WO-88/03926 A1 6/1988
WO WO 89/12685 A1 12/1989
WO WO92/01795 2/1992
WO WO-92/19636 A1 11/1992
WO WO 96/34966 A2 11/1996
WO WO 96/34966 A3 11/1996
WO WO99/33983 7/1999
WO WO01/04146 1/2001
WO WO01/07068 2/2001
WO WO-02/29045 A2 4/2002
WO WO 02/29083 A2 4/2002
WO WO 02/29083 A3 4/2002
WO WO2005/030039 4/2005
WO WO2005/038019 4/2005
WO WO2005/040367 5/2005
WO WO2006/067116 6/2006
WO WO 2006/110083 A1 10/2006
WO WO2007/065173 6/2007

OTHER PUBLICATIONS

Bandyopadhyay et al., "γ-Glutamyl carboxylation: an extracellular posttranslational modification that antedates the divergence of molluscs, anthropods, and chordates," PNAS 99(3):1264-1269 (2002).

Begley et al., "A conserved motif within the vitamin K-dependent carboxylase gene is widely distributed across animal phyla," The Journal of Biological Chemistry 275(46):36245-36249 (2000).

Cote et al., "Characterization of a stable form of human meizothrombin derived from recombinant prothrombin (R155A, R271A and R284A)," The Journal of Biological Chemistry 269(15):11374-11380 (1994).

Czerwiec et al., "Expression and characterization of recombinant vitamin K-dependent γ-glutamyl carboxylase from an invertebrate, *Conus textile*," Eur. J. Biochem 269:6162-6172 (2002).

Fischer et al., "purification of recombinant human coagulation factors II and IX and protein S expressed in recombinant Vaccinia virus-infected Vero cells," Journal of Biotechnology 38:129-136 (1995).

Hallgren et al. "Carboxylase overexpression effects full carboxylation but poor release and secretion of a factor IX: implications for the release of vitamin K-dependent proteins," Biochemistry 41:15045-15055 (2002).

Harvey et al, "Mutagenesis of the γ-carboxyglutamic acid domain of human factor VII to generate maximum enhancement of the membrane contact site," The Journal of Biological Chemistry 278(10):8363-8369 (2003).

Herlitschka et al., "Overexpression of human prothrombin in permanent cell lines using a dominant selection/amplification fusion marker," Protein Expression and Purification 8:358-364 (1996).

Jorgensen et al., "Expression of completely γ-carboxylated recombinant human prothrombin," The Journal of Biological Chemistry 262(14):6729-6734 (1987).

(Continued)

*Primary Examiner*—James S Ketter
(74) *Attorney, Agent, or Firm*—Fish & Richardson P.C.

(57) ABSTRACT

The present invention relates to methods and tools for producing large quantities of gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-carboxylated protein.

67 Claims, 2 Drawing Sheets

OTHER PUBLICATIONS

Malhotra et al., "The kinetics of activation of normal and γ-carboxyglutamic acid-deficient prothrombins," The Journal of Biological Chemistry 260(1):279-287 (1985).
Rehemtulla et al., "In vitro and in vivo functional characterization of bovine vitamin K-dependent γ-carboxylase expressed in Chinese hamster ovary cells," Proc. Natl. Acad. Sci. USA 90:4611-4615 (1993).
Roddie et al., "Haemostasis and thrombosis—Recombinant coagulation factors," Blood Reviews 11:169-177 (1997).
Russo et al., "Biologically active recombinant prothrombin and antithrombin III expressed in a human hepatoma/vaccinia virus system," Biotechnology and Applied Biochemistry 14:222-223 (1991).
Russo et al., "Stable expression and purification of a secreted human recombinant prethrombin-2 and its activation to thrombin," Protein Expression and Purification 10:214-225 (1997).
Stanley et al., "The propeptides of the vitamin K-dependent proteins possess different affinities for the vitamin K-dependent carboxylase," The Journal of Biological Chemistry 274(24):16940-16944 (1999).
Vo et al., "Undercarboxylation of recombinant prothrombin revealed by analysis of γ-carboxyglutamic acid using capillary electrophoresis and laser-induced fluorescence," Febs Letters 445:256-260 (1999).
Walker et al., "On a potential global role for vitamin K-dependent γ-carboxylation in animal systems," The Journal of Biological Chemistry 276(11):7769-7774 (2001).
Wu et al., "Cloning and expression of the cDNA for human γ-glutamyl carboxylase," Science 254:1634-1636 (1991).
Wu et al., "N-Glycosylation contributes to the intracellular stability of prothrombin precursors in the endoplasmic reticulum," Thrombosis Research 96:91-98 (1999).
PCT/SE2004/001453 International Search Report Jan. 21, 2005.
Li et al., "Identification of the gene for vitamin K epoxide reductase", *Nature* 427:541-544 (2004).
Scharrer et al., "Products used to treat hemophilia: evolution of treatment for hemophilia A and B," in: Lee et al., eds., *Textbook of Hemophilia* (New York, Blackwell, 2005), Ch. 23, pp. v-x and 131-135.
Sun et al., "Vitamin K epoxide reductase significantly improves carboxylation in a cell line overexpressing factor X," *Blood* 106 (12):3811-3815 (2005).
Wajih et al., "Engineering of a Recombinant Vitamin K-dependent γ-Carboxylation System with Enhanced γ-Carboxyglutamic Acid Forming Capacity," *J. Biol. Chem.* 280:10540-10547 (2005).
Wajih et al., "Increased Production of Functional Recombinant Human Clotting Factor IX by Baby Hamster Kidney Cells Engineered to Overexpress VKORC1, the Vitamin K 2,3-Expoxide-reducing Enzyme of the Vitamin K Cycle," *J. Biol. Chem.* 280:31603-31607 (2005).
Zhang et al., "Relative Promoter Strengths in Four Human Prostate Cancer Cell Lines Evaluated by Particle Bombardment-Mediated Gene Transfer," *The Prostate*, 51:286-292 (2002).
Bentley et al., "Differential Efficiency of Expression of Humanized Antibodies in Transient Transfected Mammalian Cells", Hybridoma, vol. 17(6), pp. 559-567 (1998).
Camire et al., "Enhanced γ-Carboxylation of Recombinant Factor X Using a Chimeric Construct Containing the Prothrombin Propeptide", Biochemistry, vol. 39, pp. 14322-14329 (2000).
Herlitschka et al., "Overexpression of Human Prothrombin in Permanent Cell Lines Using a Dominant Selection/Amplification Fusion Marker", Protein Expression and Purification, vol. 8, pp. 358-364 (1996).
Kozak, "Point Mutations Define a Sequence Flanking the AUG Initiator Codon That Modulates Translation by Eukaryotic Ribosomes", Cell, vol. 44, pp. 283-292 (1986).
Kozak, "Downstream Secondary Structure Facilitates Recognition of Intiator Codons by Eukaryotic Ribosomes", Proceedings of the National Academy of Sciences of the United States of America, vol. 87(21), pp. 8301-8305 (1990).
Kozak, "An analysis of 5'-noncoding sequences from 699 vertebrate messenger RNAs", Nucleic Acids Research, vol. 15(20), pp. 8125-8148 (1987).
Lingenfelter et al., "Isolation of the Human γ-Carboxylase and a γ-Carboxylase-Associated Protein from Factor IX-Expressing Mammalian Cells", Biochemistry, vol. 35, pp. 8234-8243 (1996).
Melcher et al., "Plasmid vectors with a 5 -hybrid intron facilitate high-level glycoprotein expression in CHO-cells", Biochimica et Biophysica Acta 1575, pp. 49-53 (2002).
Rouet et al., "A Potent Enhancer Made of Clustered Liver-specified Elements in the Transcription Control Sequences of Human α1-Microglobulin/Bikunin Gene*", The Journal of Biological Chemistry, vol. 267(29), pp. 20765-20773 (1992).
Umaña et al., "Tetracycline-Regulated Overexpression of Glycosyltransferases in Chinese Hamster Ovary Cells", Biotechnology and Bioengineering 65, pp. 542-549 (1999).
Bajaj et al. "Isolation and Characterization of Human Factor VII. Activation of Factor VII by Factor X" J. Biotechnol. 1981 (256) 253-259.
Bajaj et al. "A Simplified Procedure for Purification of Human Prothrombin, Factor IX and Factor X" Prep. Biochem. 1981 (11) 397-412.
Bishop et al. "Comparison of Recombinant Human Thrombin and Plasma-Derived Human α-Thrombin" Sem Throm Hem. 2006 (32) 86-97.
Clark et al. "The Secreted Protein Discovery Initiative (SPDI), a Large-Scale Effort to Identify Novel Human Secreted and Transmembrane Proteins: A Bioinformatics Assessment" Genome Res. 2003 (13) 2265-2270.
Fair et al. "Biosynthesis and Secretion of Factor VII, Protein C, Protein S, and the Protein C Inhibitor From a Human Hepatoma Cell Line" Blood. 1986 (67) 64-70.
Falkner et al. "High Level Expression of Active Human Prothrombin in a Vaccine Virus Expression System" Thrombosis and Haemostasis. 1992 (68) 119-124.
Hellstern et al. Preface Thrombosis Research. 1999 (95) S1.
Hellstern et al. "Prothrombin Complex Concentrates: Indications, Contraindications, and Risks: A Task Force Summary" Thrombosis Research. 1999 (95) S3-S6.
Hellstern "Production and Composition of Prothrombin Complex Concentrates: Correlation between Composition and Therapeutic Efficiency" Thrombosis Research. 1999 (95) S7-S12.
Kini et al. "The intriguing world of prothrombin activators from snake venom" Toxicon. 2005 (45) 1133-1145.
Köhler "Thrombogenicity of Prothrombin Complex Concentrates" Thrombosis Research. 1999 (95) S13-S17.
Munns et al. "Vitamin K-dependent synthesis and modification of precursor prothrombin in cultured H-35 hepatoma cells" Proc. Natl. Acad. Sci. 1976 (73) 2803-2807.
Nishida et al. "cDNA cloning and deduced amino acid sequence of prothrombin activator (ecarin) from Kenyan *Echis carinatus* venom" Biochem. 1995 (34) 1771-1778.
Pei et al. "Expression, isolation, and characterization of an active site (serine 528-alanine) mutant of recombinant bovine prothrombin" J. Biol. Chem. 1991 (266) 9598-9604.
Pejler et al. "Thrombin Is Inactivated by Mast Cell Secretory Granule Chymase" J. Biol. Chem. 1993 (268) 11817-11822.
Robertson "Genes Encoding Vitamin-K Epoxide Reductase Are Present in *Drosophila* and Trypanosomatid Protists" Genetics. 2004 (168) 1077-1080.
Rost et al. "Mutations in *VKORC1* cause warfarin resistance and multiple coagulation factor deficiency type 2" Nature. 2004 (427) 537-541.
Scharrer "The Need for Highly Purified Products to Treat Hemophilia B" Acta Haematol. 1995 (94) 2-7.
Strausberg et al. "Generation and initial analysis of more than 15,000 full-length human and mouse cDNA sequences" Proc. Natl. Acad. Sci. U.S.A. 2002 (99) 16899-16903.
Tans et al. "Prothrombin Activation by Snake Venom Proteases" J. Toxicol.-Toxin Reviews. 1993 (12) 155-173.
Wallin et al. "Vitamin K-dependent Carboxylation and Vitamin K Metabolism in Liver" J. Clin. Invest. 1985 (76) 1879-1884.
Wallin et al. "Vitamin K 2,3-epoxide reductase and the vitamin K-dependent γ-carboxylation system" Thrombosis Research. 2003 (108) 221-226.

Wang et al. "The Growth Inhibitory Effects of Vitamins K and Their Actions on Gene Expression" Hepatology. 1995 (22) 876-881.
Yonemura et al. "Preparation of recombinant α-thrombin: high-level expression of recombinant human prethrombin-2 and its activation by recombinant ecarin" J. Biochem. 2004 (135) 577-582.
Restriction Requirement in U.S. Appl. No. 11/572,870, mailed Apr. 2, 2009, 5 pages.
Restriction Requirement in U.S. Appl. No. 12/167,614, mailed Apr. 6, 2009, 8 pages.
Broun et al. "Catalytic Plasticity of Fatty Acid Modification Enzymes Underlying Chemical Diversity of Plant Lipids" Science. 1998 (282) 1315-1317.
Kaufman et al. "Expression, Purification, and Characterization of Recombinant γ-Carboxylated Factor IX Synthesized in Chinese Hamster Ovary Cells" J. Biol. Chem. 1986 (261) 9622-9628.
Lucas et al. "High-level production of recombinant proteins in CHO cells using a dicistronic DHFR intron expression vector" Nucleic Acids Research. 1996 (24) 1774-1779.
Sadler "K is for koagulation" Nature. 2004 (427) 493-494.
Seffernick et al. "Melamine Deaminase and Atrazine Chlorohydrolase: 98 Percent Identical but Functionally Different" J. Bacteriol. 2001 (183) 2405-2410.
Wajih et al. "The Inhibitory Effect of Calumenin on the Vitamin K-dependent γ-Carboxylation System" J. Biol. Chem. 2004 (279) 25276-25283.
Whisstock et al. "Prediction of protein function from protein sequence and structure" Q. Rev. Biophysics. 2003 (36) 307-340.
Witkowski et al. "Conversion of β-Ketoacyl Synthase to a Malonyl Decarboxylase by Replacement of the Active-Site Cysteine with Glutamine" Biochemistry. 1999 (38) 11643-11650.
Fish & Richardson P.C., Response to Restriction Requirement and Preliminary Amendment dated Apr. 2, 2009 in U.S. Appl. No. 11/572,870, filed Sep. 25, 2009, 16 pages.
Fish & Richardson P.C., Amendment in Reply to Restriction Requirement dated Apr. 6, 2009 in U.S. Appl. No. 12/167,614, filed Aug. 4, 2009, 9 pages.
USPTO Non-Final Office Action in U.S. Appl. No. 12/167,614, mailed Sep. 29, 2009, 19 pages.
Gustafsson et al., "Codon bias and heterologous protein expression" Trends in Biotechnol., 22(7):346-353 (2004).
Koresawa et al., "Synthesis of a new cre recombinase gene based on optimal codon usage for mammalian systems" J. Biochem., 127:367-372 (2000).
McCawley et al., "Matrix metalloproteinases: they're not just for matrix anymore!" Curr. Opinion Cell Biol., 13:534-540 (2001).
Newby A.C., "Matrix metalloproteinases regulate migration, proliferation, and death . . . " Cardiovascular Res., 69:614-624 (2006).
Gamma Glutamyl Carboxylase. UniPro Database. [online], [retrieved on Jan. 14, 2010] Retrieved from the UniPro Database using Internet <URL: http://www.uniprot.org/uniprot/?query=gamma+glutamyl+carboxylase&sort=score>.
Himmelspach et al. "A Fully Recombinant Partial Prothrombin Complex Effectively Bypasses fVII In Vitro and In Vivo" Thromb Haemost. 2002 (88) 1003-1011.
Slimko et al. "Codon optimization of *Caenorhabditis elegans* GluCl ion channel genes for mammalian cells dramatically improves expression levels" J. Neuroscience Methods. 2003 (124) 75-81.
PCT Written Opinion for Application No. PCT/SE2008/050836, dated Jan. 21, 2010, 10 pages.
Nucleotide sequence of human prothrombin (EBI accession No. AJ972449). Last modified Oct. 21, 2008, 8 pages.
Amino acid sequence for wild type ecarin (EBI accession No. Q90495). Last modified Jan. 19, 2010, 5 pages.

* cited by examiner

METHODS FOR PRODUCING GAMMA-CARBOXYLATED PROTEINS

RELATED APPLICATIONS

This application claims priority to Great Britain Application No. 0324044.7, filed Oct. 14, 2003, the entire contents of which is hereby incorporated by reference.

TECHNICAL FIELD

The present invention relates a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter. The invention further relates to a method of producing a protein requiring gamma-carboxylation in high yields.

BACKGROUND TO THE INVENTION

Bleeding is a common clinical problem. It is a consequence of disease, trauma, surgery and medicinal treatment. It is imperative to mechanically stop the bleeding. This may be difficult or even impossible due to the location of the bleeding or because it diffuses from many (small) vessels. Patients who are bleeding may thus require treatment with agents that support haemostasis. This may be blood-derived products (haemotherapy), agents that cause the release of endogenous haemostatic agents, recombinant coagulation factors (F), or agents that delay the dissolution of blood clots.

The first line treatment among the blood derived products, often obtained from the local hospital, are whole blood for volume substitution and support of haemostasis, packed red cells for the improvement of oxygen transporting capacity, platelet concentrates to raise the number of platelets (if low or defective) and fresh frozen plasma for support of the haemostasis (blood coagulation and platelet aggregation). Second line plasma derived products that support haemostasis are plasma cryoprecipitate, prothrombin complex concentrates, activated prothrombin complex concentrates and purified coagulation factors. Several coagulation factors are today available as human recombinant proteins, inactive (coagulation factors VIII and IX) and activated (coagulation factor VIIa).

Haemophilia is an inherited or acquired bleeding disorder with either abnormal or deficient coagulation factor or antibodies directed towards a coagulation factor which inhibits the procoagulant function. The most common haemophilias are haemophilia A (lack coagulation factor VIII) and haemophilia B (factor IX). The purified or recombinant single coagulation factors are the main treatment of patients with haemophilia. Patients with inhibitory antibodies posses a treatment problem as they may also neutralise the coagulation factor that is administered to the patient. The active form of Protein C (APC) is an inhibitor of plasma coagulation by degradation of the activated coagulation factors Va and VIIIa. Recombinant APC has been shown to be an effective treatment of undue plasma coagulation in patients with sepsis.

Coagulation factors for therapeutic use can be obtained from human plasma, although the purification process is not simple and requires many steps of which several aim at eliminating contaminating viruses. But even with extensive safety measures and testing of blood-derived products, contamination with infectious viruses or prions cannot be ruled out. Because of this risk it is highly desirable to produce human therapeutic proteins from recombinant cells grown in media without animal derived components. This is not always straightforward as many proteins require a mammalian host to be produced in a fully functional form, i.e. be correctly post-translationally modified. Among the coagulation factors commercially produced in recombinant cells are FVII (NovoSeven), FVIII (Kogenate, Recombinate, Refacto) and FIX (BeneFix) (Roddie and Ludlam. Blood Rev. 11: 169-177, 1997) and Active Protein C (Xigris). One of the major obstacles in obtaining large amounts of fully functional recombinant human coagulation factors lies in the Gla-domain present in FII, FVII, FIX, FX and Protein C. This domain contains glutamic acid residues that are post-translationally modified by addition of carboxyl groups. The production of these factors are hampered by the fact that over-expression of them result in under-carboxylated, and hence inactive, protein. The Gla modifications are a result of the action of a vitamin K-dependent enzyme called γ-glutamyl carboxylase (GGCX). This enzyme has been extensively studied by many scientists, particularly those involved in coagulation factor research (WO-A-8803926; Wu et al. Science 254(5038): 1634-1636, 1991; Rehemtulla et al., Proc Natl Acad Sci USA 90: 4611-4615, 1993; Stanley J. Biol. Chem. 274(24): 16940-16944, 1999; Vo et al., FEBS letters 445: 256-260, 1999; Begley et al., The Journal of Biological Chemistry 275(46): 36245-36249, 2000; Walker et al., The Journal of Biological Chemistry 276(11): 7769-7774, 2001; Bandyopadhyay, et al. Proc Natl Acad Sci USA 99(3): 1264-1269, 2002; Czerwiec et al., Eur J Biochem 269: 6162-6172, 2002; Hallgren et al., Biochemistry 41(50): 15045-15055, 2002; Harvey et al., The Journal of Biological Chemistry 278(10): 8363-8369, 2003). Attempts to increase yields by co-expressing GGCX with coagulation factor FIX has been tried by at least two scientific groups but were not successful (Rehemtulla, et al. 1993, ibid; Hallgren et al. 2002, ibid). Considering the large interest in γ-carboxylated proteins, it may be assumed that many more co-expression trials have failed and thus have not been reported.

For human FII (prothrombin) at least 8 out of 10 Glu residues have to be correctly modified in order to obtain fully functional prothrombin (Malhotra, et al., J. Biol. Chem. 260: 279-287, 1985; Seegers and Walz 'Prothrombin and other vitamin K proteins', CRC Press, 1986). Extensive efforts to obtain high production levels of rhFII have been made using several different systems such as CHO cells, BHK cells, 293 cells and vaccinia virus expression systems, but have all failed or resulted in an under-carboxylated product and thus functionally inactive prothrombin (Jørgensen et al., J. Biol. Chem. 262: 6729-6734, 1987; Russo et al., Biotechnol Appl Biochem 14(2): 222-233, 1991; Fischer et al., J Biotechnol 38(2): 129-136, 1995; Herlitschka et al. Protein Expr. Purif. 8(3): 358-364, 1996; Russo et al., Protein Expr. Purif. 10: 214-225, 1997; Vo et al. 1999, ibid; Wu and Suttie Thromb Res 96(2): 91-98, 1999). Earlier reported productivities for carboxylated recombinant human prothrombin are low; 20 mg/L for mutant prothrombin (Cote et al., J. Biol. Chem 269: 11374-11380, 1994), 0.55 mg/L for human prothrombin expressed in CHO cells (fully carboxylated, Jørgensen et al. 1987, ibid), 25 mg/L in CHO cells (degree of carboxylation not shown, Russo et al. 1997, ibid).

WO 92/19636 discloses the cloning and sequence identification of a human and bovine vitamin K dependent carboxylase. The application suggests co-expressing the vitamin K dependent carboxylase and a vitamin K dependent protein in a suitable host cell in order to prepare the vitamin K dependent protein. No co-expression of the carboxylase and vitamin K dependent protein is exemplified.

There is a need for improved methods to produce activated blood clotting factors in high yields. The present invention sets out to address this need.

SUMMARY OF THE INVENTION

According to a first aspect of the invention there is provided a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1.

According to another aspect of the invention there is provided a cell which is engineered to express (i) a protein which requires gamma-carboxylation, and (ii) a γ-glutamyl carboxylase, wherein the proteins (i) and (ii) are expressed in a ratio between 10:1 and 500:1.

According to another aspect of the invention there is provided genetically modified eukaryotic host cell comprising:

(i) a polynucleotide sequence encoding γ-glutamyl carboxylase protein wherein said γ-glutamyl carboxylase protein encoding sequence is operably linked to expression control sequences permitting expression of γ-glutamyl carboxylase protein by said cell; and (ii) a polynucleotide encoding a protein requiring carboxylation by the γ-glutamyl carboxylase protein operably linked to expression control sequences permitting expression of said protein requiring carboxylation by said cell;

wherein the cell is capable of expressing the γ-glutamyl carboxylase protein and the protein requiring carboxylation in the ratio of at least 1:10.

According to a further aspect of the invention there is provided a vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1.

According to yet another aspect of the invention there is provided a method for producing gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-carboxylated protein. In one embodiment the method is used for producing gamma-carboxylated human Factor IX and in another embodiment the method is used for producing gamma-carboxylated human prothrombin. In another embodiment, the gamma-carboxylated protein produced is human gamma-carboxylated Factor X.

According to another aspect of the invention there is provided a method for production of a gamma-carboxylated protein in a mammalian cell line, comprising the step of co-expressing with said protein requiring gamma-carboxylation in the mammalian cell line a γ-glutamyl carboxylase, wherein the amount of expressed protein requiring gamma-carboxylation is at least 10-fold greater than the amount of expressed γ-glutamyl carboxylase, and (ii) isolating gamma-carboxylated protein. In one embodiment the method is used for producing gamma-carboxylated human Factor IX and in another embodiment the method is used for producing gamma-carboxylated human prothrombin. In another embodiment, the gamma-carboxylated protein produced is human gamma-carboxylated Factor X.

According to a further aspect of the invention there is provided isolated gamma-carboxylated protein produced according to the above methods, and the use of isolated gamma-carboxylated protein produced according to the above methods in coagulation therapy or the use of isolated gamma-carboxylated protein produced according to the above methods for the manufacture of a medicament for use in coagulation therapy.

According to yet a further aspect of the invention there is provided a method of producing a pharmaceutical composition suitable for inducing blood clotting or promoting increased or decreased coagulation, comprising purifying active carboxylated protein expressed from a host cell adapted to express a protein requiring gamma-carboxylation and γ-glutamyl carboxylase in a ratio of between 10:1 and 500:1 and admixing the purified carboxylated protein with one or more pharmaceutically acceptable carriers or excipients and a pharmaceutical composition obtainable from the method. In one embodiment the active carboxylated protein is gamma-carboxylated human Factor IX and in another embodiment the active carboxylated protein is gamma-carboxylated human prothrombin. In another embodiment, the active carboxylated protein is gamma-carboxylated Factor X.

DETAILED DESCRIPTION OF THE INVENTION

Figure 1A:
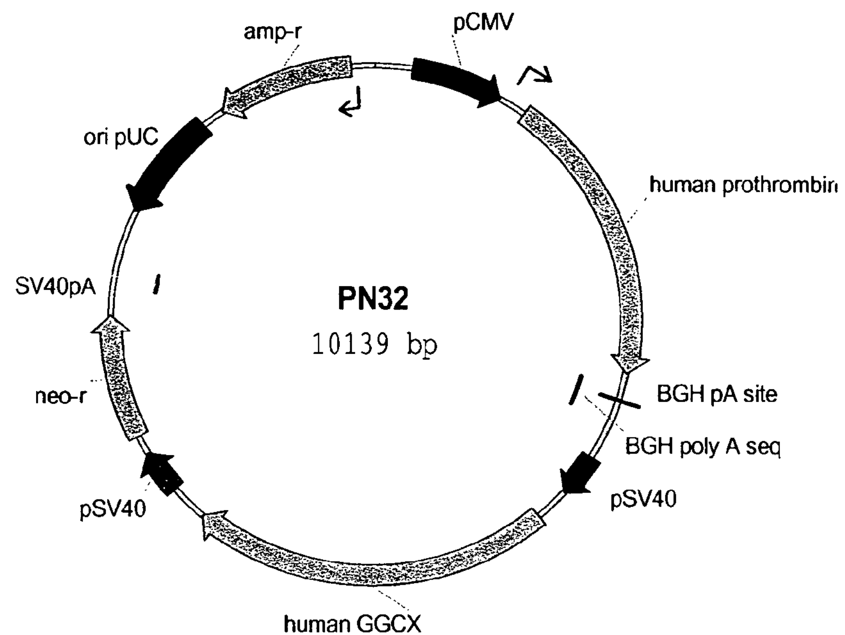
FIG. 1*a* illustrates a plasmid map of PN32 (prothrombin+GGCX) co-expression vector.

We have devised a different approach for expression of appropriately carboxylated recombinant vitamin K dependent coagulation factors at high levels, which involves co-expression of the vitamin K dependent coagulation factor and a γ-glutamyl carboxylase (GGCX) in a differential ratio. As one example we have expressed human prothrombin (rhFII) and human GGCX. Instead of using strong promoters for both rhFII and GGCX as others have tried (Rehemtulla et al., 1993, ibid; Hallgren et al., 2002, ibid), we used a strategy aiming at strong expression of FII in combination with weak or very weak expression of the GGCX, such that the amount of expressed GGCX was less than $1/10^{th}$ of the expressed rhFII. To our surprise this strategy led to high levels of secreted correctly modified rhFII and good viability of the host cells, even when the cells were grown in animal component free chemically defined medium.

We have cloned GGCX and human prothrombin into an expression vector in such a way that the prothrombin mRNA level exceeds that of GGCX mRNA by a factor of at least 10.

This results in production of a large excess of prothrombin protein compared to GGCX protein.

As a further example we have expressed rhFIX using the same GGCX co-expression vectors. This resulted in cell lines producing factor IX mRNA at levels exceeding GGCX mRNA levels by a factor of at least 10 in one case. In another cell line the factor IX: GGCX mRNA ratio was approximately 4-5:1. Only the cell line giving a ratio of at least 10:1 showed substantially increased rhFIX productivity (Table 1).

According to a further aspect of the invention there is provided a nucleic acid according to SEQ ID NO: 14 and SEQ ID NO: 15.

According to a further aspect of the invention there is provided host cells transfected or transformed with a vector comprising the sequence of SEQ. ID NO: 14 or SEQ ID NO: 15 for the expression of human Factor IX.

According to a further aspect of the invention there is provided a host cell capable of expressing human coagulation

TABLE 1

Summary of productivity and carboxylated protein:GGCX mRNA ratio

| CLONE NAME/CONSTRUCT | PROTEIN PRODUCED | PRODUCTION* OF FULLY ACTIVE PROTEIN (mg/l) | CARBOXYLATED PROTEIN:GGCX, APPROX. mRNA RATIO | SOURCE OF DATA |
|---|---|---|---|---|
| P1E2/PN32 | Human | 40 | 250:1 | Example 3 |
| B2F4/PP6 | prothrombin | 26 | 50:1 | Example 5 |
| H3B10/PP6 | | 30 | 30:1 | Example 5 |
| E1A9/PText5 | | 3.5 | No GGCX | Example 3 |
| N4D5/F9NopA | Human FIX | 7.3 | 45:1 | Example 7 |
| P1G9/F9hglx | | 1.3 | 4:1 | Example 7 |
| IC4 | | 1¤ | No GGCX | Rehemtulla 1993, U.S. Pat. No. 5,460,950 |

*Productivity was measured from spinner cultures under similar growth conditions.

¤Data from Rehemtulla 1993 and U.S. Pat. No. 5,460,950.

The vitamin K dependent coagulation factors (FII, FVII, FIX, FX and their activated forms FIIa or thrombin, FVIIa, FIXa, FXa) produced by the present method of co-expression with GGCX can be expected to be useful in the prevention and treatment of bleeding following trauma, surgery or diseases of the liver, kidneys, platelets or blood coagulation factors (haemophilia). Likewise the coagulation factor Protein C and its activated form APC can be expected to be useful in the prevention and treatment of disorders of increased coagulation with or without decreased levels of Protein C. The method is also applicable to other proteins that require post-translational carboxylation.

According to a first aspect of the invention there is provided a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1.

In a preferred embodiment the ratio of the expressed proteins is between 10:1 and 1000:1, more preferably between 10:1 and 500:1 and still more preferably between 25:1 and 250:1. A particularly suitable ratio is around 200:1.

In separate embodiments the ratio of the two expressed proteins can be at least 10:1, 30:1, 45:1, 50:1, 100:1, 200:1, 250:1, 300:1, 400:1, 500:1 and 1000:1.

In one particular embodiment, both the nucleic acid molecule encoding the protein requiring gamma-carboxylation and associated expression control sequences, and the nucleic acid molecule encoding the γ-glutamyl carboxylase and associated expression control sequences are located on the same expression vector. In another embodiment these two nucleic acid molecules are located on separate expression vectors.

factor IX and human gamma carboxylase enzymes, wherein the nucleic acid encoding the human coagulation factor IX and the nucleic acid encoding the gamma carboxylase are operably linked to control sequences that are capable of expressing the two proteins in a ratio of at least 10:1, respectively.

According to a further aspect of the invention there is provided a non-human eukaryotic host cell adapted to express human coagulation factor IX and human gamma carboxylase enzymes in a ratio of at least 10:1. In a particular embodiment, the nucleic acid encoding the human coagulation factor IX and the nucleic acid encoding the gamma carboxylase are operably linked to control sequences that are capable of expressing the two proteins in a ratio of at least 10:1, respectively.

According to a further aspect of the invention there is provided a host cell harbouring exogenous nucleic acid comprising human coagulation factor IX encoding nucleic acid under the control of hCMV promoter and human carboxylase encoding nucleic acid under the control of SV40 promoter.

According to a further aspect of the invention there is provided a nucleic acid according to SEQ. ID NO: 1, SEQ. ID NO: 2 or SEQ ID NO: 3.

According to a further aspect of the invention there is provided host cells transfected or transformed with a vector comprising the sequence of SEQ. ID NO: 1, SEQ. ID NO: 2 or SEQ ID NO: 3 for the expression of human prothrombin.

According to a further aspect of the invention there is provided host cells capable of expressing human prothrombin and human gamma carboxylase enzymes, wherein the nucleic acid encoding the human prothrombin and the nucleic acid encoding the gamma carboxylase are operably linked to control sequences that are capable of expressing the two proteins in a ratio of at least 10:1, respectively.

According to a further aspect of the invention there is provided a non-human eukaryotic host cell adapted to express human prothrombin and human gamma carboxylase enzymes in a ratio of at least 10:1. In a particular embodiment, the nucleic acid encoding the human prothrombin and the nucleic acid encoding the gamma carboxylase are operably linked to control sequences that are capable of expressing the two proteins in a ratio of at least 10:1, respectively.

According to a further aspect of the invention there is provided a host cell harbouring exogenous nucleic acid comprising human prothrombin encoding nucleic acid under the control of hCMV promoter and human carboxylase encoding nucleic acid under the control of SV40 promoter.

The invention has been exemplified using prothrombin and coagulation factor IX as the proteins requiring carboxylation. However, several proteins other than prothrombin and factor IX are dependent on correct γ-carboxylation for their full biological activity. Among those known from man are the coagulation factor FVII, which at present is only commercially produced in recombinant mammalian cells at relatively low levels (approximately 10 mg/L or less). The present invention will be applicable to improve the productivity of any protein that is dependent on γ-carboxylation, such proteins include, but are not limited to: prothrombin, coagulation factor II (FII), coagulation factor VII (FVII), coagulation factor IX (FIX), coagulation factor X (FX), Protein C, Protein S, Protein Z, Bone Gla protein (also known as: BGP or osteocalcin), Matrix Gla protein (MGP), proline rich Gla polypeptide 1 (PRRG1), proline rich Gla polypeptide 2 (PRRG2), Growth arrest-specific protein 6 (Gas 6). Other suitable proteins are: FXa-like protein in venom of elapid snake (subfamily Acanthophiina) and cone snail venom (*Conus textile*).

Each of these proteins, including their nucleic acid and amino acid sequences, are well known. Table 2 identifies representative sequences of wild-type and mutant forms of the various proteins that can be used in the present invention.

TABLE 2

| DESCRIPTION | CDNA EMBL ACC# | SPLICE VARIANTS (PROTEIN) | MUTATIONS | GENE EMBL ACC# |
|---|---|---|---|---|
| Glutamate gamma carboxylase | BC013979 | 2; BC013979; AF253530 | 1 SNP (EMBL# U65896); 2 SNPs (OMIM# 137167) | U65896 |
| Prothrombin | V00595 | 1; V00595 | approx. 100 SNP's (EMBL# AF478696) | AF478696 |
| Factor VII | AF466933 | 4; AF466933; AF272774; AR030786; AAN60063 | 21 SNPs (OMIM# 277500) | J02933 |
| Factor IX | A01819 | 3; A01819; A34669; M19063 | 5 SNPs (EMBL# AF536327); 108 SNPs (OMIM# 306900) | AF536327 |
| Factor X | BC046125 | 4; BC040125; M57285; AR095306; AB005892 | 118 SNPs (EMBL# AF503510); 14 SNPs (OMIM# 227600) | AF503510 |
| Protein C | BC034377 | 7; AB083690; AB083693; I09623; S50739; S72338 | 57 SNPs (EMBL# AF378903); 25 SNPs (OMIM# 176860) | AF378903 |
| Osteocalcin | AF141310 | 5; AF141310; AF141310; BC033656; X04143; X51699 | | X04143 |
| Matrix GLA protein | BC005272 | 1; BC005272 | | |
| Growth arrest-specific 6; AXL stimulatory factor | BC038984 | 1; BC038984 | | |
| Protein Z | M55670 | 2; AB033749; AB033749 | | |
| Proline-rich Gla (G-carboxyglutamic acid) polypeptide 1 | AF009242 | 2; AF009242;BC030786 | | |
| Proline-rich Gla (G-carboxyglutamic acid) polypeptide 2 | AF009243 | 2; AF009243; BC026032 | | |
| Vitamin K-dependent protein S precursor | BC015801 | 1; BC015801 | approx. 100 SNPs (EMBL# AY308744); 8 SNPs (OMIM# 176880) | AY308744 |

It will be appreciated that the invention is not restricted to a particular protein or protein encoding sequence of one of these proteins to be co-expressed. Moreover, and in particular with respect to blood coagulation factors, numerous mutant forms of the proteins have been disclosed in the art. The present invention is equally applicable to these mutant forms, including naturally occurring allelic variants, of the proteins as it is to wild-type sequence. In one embodiment the invention can be undertaking with any wild-type protein or one with at least 90%, preferably at least 95% sequence identity thereto.

The sequence identity between two sequences can be determined by pair-wise computer alignment analysis, using programs such as, BestFit, PILEUP, Gap or FrameAlign. The preferred alignment tool is BestFit. In practise, when searching for similar/identical sequences to the query search, from within a sequence database, it is generally necessary to perform an initial identification of similar sequences using suitable algorithms such as Blast, Blast2, NCBI Blast2, WashU Blast2, FastA, or Fasta3, and a scoring matrix such as Blosum 62. Such algorithms endeavour to closely approximate the "gold-standard" alignment algorithm of Smith-Waterman. Thus, the preferred software/search engine program for use in assessing similarity, i.e., how two primary polypeptide sequences line up is Smith-Waterman. Identity refers to direct matches, similarity allows for conservative substitutions.

The term "γ-glutamyl carboxylase" or "GGCX", as used herein, refers to a vitamin K dependent enzyme that catalyses carboxylation of glutamic acid residues.

GGCX enzymes are widely distributed, and have been cloned from many different species such as the beluga whale *Delphinapterus leucas*, the toadfish *Opsanus tau*, chicken (*Gallus gallus*), hagfish (*Myxine glutinosa*), horseshoe crab (*Limulus polyphemus*), and the cone snail *Conus textile* (Begley et al., 2000, ibid; Bandyopadhyay et al. 2002, ibid). The carboxylase from conus snail is similar to bovine carboxylase and has been expressed in COS cells (Czerwiec et al. 2002, ibid). Additional proteins similar to GGCX can be found in insects and prokaryotes such as *Anopheles gambiae, Drosophila melanogaster* and *Leptospira* with NCBI accession numbers: gi 31217234, gi 21298685, gi 24216281, gi 24197548 and (Bandyopadhyay et al., 2002, ibid), respectively. The carboxylase enzyme displays remarkable evolutionary conservation. Several of the non-human enzymes have shown, or may be predicted to have, activity similar to that of the human GGCX we have used, and may therefore be used as an alternative to the human enzyme.

Table 3 identifies representative sequences of predicted proteins homologous to human GGXC (sorted after species origin) that can be used in the present invention.

TABLE 3

| Species | Data base accession #/ID |
|---|---|
| *Homo sapiens* (man) | NM_000821.2 |
| | HUMGLUCARB |
| | HUMHGCA |
| | BC004422 |
| | HSU65896 |
| | AF253530.1 |
| *Papio hamadryas* (red baboon) | AC116665.1 |
| *Delphinapterus leucas* (white whale) | AF278713 |
| *Bos taurus* (bovine) | NM_174066.2 |
| | BOVCARBOXG |
| | BOVBGCA |
| *Ovis aries* (domestic sheep) | AF312035 |
| *Rattus norvegicus* (brown rat) | NM_031756.1 |
| | AF065387 |
| *Mus musculus* (mouse) | NM_019802.1 |
| | AF087938 |
| *Opsanus tau* (bony fishes) | AF278714.1 |
| *Conus textile* (molluscs) | AY0044904.1 |
| | AF382823.2 |
| *Conus imperialis* (molluscs) | AF448234.1 |
| *Conus episcopatus* (molluscs) | AF448233.1 |
| *Conus omaria* (molluscs) | AF448235.1 |
| *Drosophila melanogaster* (fruit fly) | NM_079161.2 |
| *Anopheles gambiae* (mosquito) | XM_316389.1 |
| *Secale cereale* (monocots) | SCE314767 |
| *Triticum aestivum* (common wheat) | AF280606.1 |
| *Triticum urartu* (monocots) | AY245579.1 |
| *Hordeum vulgare* (barley) | BLYHORDCA |
| *Leptospira interrogans* (spirochetes) | AE011514.1 |
| *Streptomyces coelicolor* (high GC Gram+ bacteria) | SCO939109 |
| | SCO939124 |
| | AF425987.1 |
| *Streptomyces lividans* (high GC Gram+ bacteria) | SLU22894 |
| *Streptomyces viginiae* (high GC Gram+ bacteria) | SVSNBDE |
| *Micrococcus luteus* (high GC Gram+ bacteria) | MLSPCOPER |
| *Chlamydomonas reinhardtii* (green algae) | AF479588.1 |
| *Dictyostelium discoideum* (slime mold) | AC115612.2 |
| *Coturnix coturnix* (birds) | AF364329.1 |
| *Bradyrhizobium japonicum* (α-protoebacteria) | AP005937.1 |
| *Rhodobacter sphaeroides* (α-proteobacteria) | RSY14197 |
| *Sinorhizobium meliloti* (α-proteobacteria) | RME603647 |
| | AF119834 |
| *Mesorhizobium loti* (α-proteobacteria) | AP003014.2 |
| *Chromobacterium violaceum* (β-proteobacteria) | AE016910.1 |
| | AE016918.1 |
| *Pseudomonas aeruginosa* (γ-proteobacteria) | AE004613.1 |
| | AF165882 |
| *Xanthomonas axonopodis* (γ-proteobacteria) | AE011706.1 |
| Human herpesvirus 8 | KSU52064 |
| | KSU75698 |
| | AF305694 |
| | AF360120 |
| | AF192756 |

Each of the above-identified GGCX proteins and GGCX proteins from other species can be used as the carboxylase enzyme in the present invention.

One way to effect differential expression of the two co-expressed proteins is to use different promoters as part of the respective expression control sequences. The art is replete with examples of different promoters and other expression control sequences that are capable of expressing heterologous proteins to differing degrees or extents. Recombinant expression technology is suitably advanced such that a person skilled in the art of protein expression is able to select promoters and other control sequences to bring about co-expression of the protein requiring carboxylation and the carboxylase in the desired ratio. The selection of which particular promoters and other expression control sequences to use is a matter of individual choice.

In one embodiment, the control sequences associated with the protein requiring gamma-carboxylation comprise a strong promoter. In one embodiment this is the human cytomegalovirus (hCMV) immediate-early promoter. A strong promoter is here defined as a promoter giving rise to more than 1000 transcripts/cell. A weak promoter is here defined as a promoter giving rise to less than 1000 transcripts/cell.

In another embodiment, the control sequences associated with the γ-glutamyl carboxylase comprise a weak promoter. In one embodiment this is SV40 early promoter. In another embodiment the protein requiring gamma-carboxylation and the γ-glutamyl carboxylase are under the control of different promoter elements with the promoter controlling expression of the γ-glutamyl carboxylase being weaker that the promoter controlling expression of the protein requiring gamma-carboxylation.

In another embodiment, the γ-glutamyl carboxylase is under the control of SV40 early promoter and the protein requiring gamma-carboxylation is under the control of the human cytomegalovirus (hCMV) immediate-early promoter. In one embodiment according to this particular aspect of the invention the protein requiring gamma-carboxylation is human Factor X. In another embodiment the protein requiring gamma-carboxylation is human prothrombin. In another embodiment the protein requiring gamma-carboxylation is human Factor IX.

The invention has been exemplified by use of the strong CMV promoter (Boshart et al. Cell 41: 521-530, 1985) to over-express Factor 1× or prothrombin and the weaker SV40 promoter (Wenger et al. Anal Biochem 221: 416-418, 1994) to control the GGCX expression. Other strong promoter that could be used according to the present invention include, but are not limited to, pEF-1α [human elongation factor-1α subunit gene) (Mizushima and Nagata, Nuc Acids Res 18: 5322, 1990; Goldman et al., BioTechniques 21: 1013-1015, 1996), pRSV [Rous sarcoma virus (Gorman et al., Proc Natl Acad Sci USA 79: 6777-6781, 1982)] and pUbC [human ubiquitin (Schorpp et al., Nuc Acids Res 24: 1787-1788, 1996)].

It is important to ensure that the protein to be produced (protein requiring carboxylation) is in excess compared to the modification enzyme, giving a ratio of at least 10:1. Ways to achieve a low level expression of the modification enzyme (γ-glutamyl carboxylase) include:

1) Use of a weak promoter to control expression of the modification enzyme including, but not limited to, SV40 immediate early promoter, the minimized FIX promoter (Rouet et al., The Journal of Biological Chemistry 267: 20765-20773, 1992) or the HSV Thymidine kinase promoter (Wenger et al., 1994, ibid).

2) Mutate promoter or enhancer sequences of a strong promoter to reduce promoter strength.

3) Remove or change the Kozak sequence (translation initiation signal) to reduce the translation efficiency (Kozak. Nuc Acids Res 15:8125-8148, 1987; Kozak. Proc Natl Acad Sci USA 87:8301-8305, 1990).

4) Clone nucleic acid encoding protein to be produced (protein requiring carboxylation) and nucleic acid encoding GGCX on separate vectors and transfect with a large excess of the construct containing the protein to be produced so as to generate a cell with multiple copies of the construct containing the protein to be produced.

5) Clone DNA encoding protein to be produced and DNA encoding GGCX modification vectors on separate vectors, co-transfect or separately transfect, and use an amplification system to amplify the expression of the protein to be produced.

6) Isolate a stable cell line recombinantly expressing low levels of GGCX (but above endogenous levels) and use as host cell line for expression of proteins in need of γ-carboxylation.

7) Introduce mutation(s) into the GGCX in order to decrease GGCX substrate affinity.

In addition to these, the person skilled in the art of recombinant protein expression will be aware of other methods that could be used to generate a host cell that expresses the protein requiring carboxylation and the carboxylase protein in a ratio of at least 10:1.

According to a further aspect of the invention there is provided a cell which is engineered or adapted to express (i) a protein which requires gamma-carboxylation, and (ii) a γ-glutamyl carboxylase, wherein the proteins (i) and (ii) are expressed in a ratio between 10:1 and 500:1. In a particular embodiment the γ-glutamyl carboxylase is expressed between 2 and 5-fold above endogenous levels (i.e. that in a non-engineered or adapted cell).

According to a further aspect of the invention there is provided a recombinant cell adapted to express (i) γ-glutamyl carboxylase protein above constitutive levels found in an equivalent unadapted cell and (ii) a protein requiring carboxylation, wherein the amount of expressed γ-glutamyl carboxylase protein and protein requiring carboxylation is in the ratio of at least 1:10.

According to a further aspect of the invention there is provided a genetically modified eukaryotic host cell comprising:

(i) a polynucleotide sequence encoding γ-glutamyl carboxylase protein wherein said γ-glutamyl carboxylase protein encoding sequence is operably linked to expression control sequences permitting expression of γ-glutamyl carboxylase protein by said cell; and (ii) a polynucleotide encoding a protein requiring carboxylation by the γ-glutamyl carboxylase protein operably linked to expression control sequences permitting expression of said protein requiring carboxylation by said cell;

wherein the cell is capable of expressing the γ-glutamyl carboxylase protein and the protein requiring carboxylation in the ratio of at least 1:10.

According to a further aspect of the invention there is provided a cell adapted to express a protein which requires gamma-carboxylation and γ-glutamyl carboxylase, wherein the nucleic acid encoding the protein which requires gamma-carboxylation and the nucleic acid encoding the γ-glutamyl carboxylase are under the control of regulatory sequences suitable for ensuring that the amount of expressed protein which requires gamma-carboxylation is at least 10-fold the amount of the γ-glutamyl carboxylase protein.

In one embodiment, at least one of the protein which requires gamma-carboxylation and the γ-glutamyl carboxylase is expressed from nucleic acid that has been introduced into the cell by recombinant technology. An alternate way of working the invention is to express endogenous protein (protein requiring carboxylation or carboxylase), but with substitution of the endogenous control sequences (promoter etc.) with heterologous sequences to effect the desired level of expression.

The host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NSO, 293, Per C.6, BHK and COS cells, and derivatives thereof. In one embodiment the host cell is the mammalian cell line CHO-S.

Overexpression of carboxylation dependent proteins has earlier generally resulted in undercarboxylated products. This is due to the endogenous host cell carboxylation capacity is being limited. On the other hand vast (16 to 70-fold) over expression of GGCX activity does not improve product yield (Rehemtulla et al., Proc Natl Acad Sci USA 90: 4611-4615, 1993), (Berkner and Pudota, Proc Natl Acad Sci USA. 95: 446-471, 1998), (Hallgren et al., Biochemistry 41(50): 15045-15055, 2002). The reason for this is not fully understood. Our invention requires a moderate over expression of GGCX. This ensures that greater than endogenous levels of GGCX are expressed from the cell, for example, where the GGCX activity level is elevated only 1.5 to 5-fold. At this moderately elevated level, surprisingly high levels of fully carboxylated rhFII were obtained as shown in Example 1.

It will therefore be appreciated that the expression ratio of the protein requiring carboxylation and the carboxylase that distinguishes this invention from previous co-expression teachings, excludes levels of GGCX that are endogenously produced. To meet the high productivity required it is necessary to express the carboxylase and the protein requiring carboxylation at levels above those found in normal cells.

In a preferred embodiment a cell or cell line is used which has little or no constitutively expressed carboxylase and/or protein requiring carboxylation.

In one embodiment the γ-glutamyl carboxylase is expressed at less than or equal to 10% of the amount of the protein which requires gamma-carboxylation. In alternate, further embodiments the γ-glutamyl carboxylase is expressed at less than or equal to 5%, 2%, 1%, 0.5%, 0.25% 0.1%, 0.05% or 0.01% of the amount of the protein which requires gamma-carboxylation.

The degree expression of the two proteins can be measured using techniques familiar to a person skilled in the art. These include direct measurements, for example measuring biological activity of the protein, or amount of protein (e.g. using antibodies), or indirect measurements, for example via measurement of mRNA transcript levels (e.g. Taqman analysis as in Example 3). The following references disclose ways of measuring GGCX enzyme activity (Lingenfelter et al., Biochemistry 35: 8234-8243, 1996; Berkner et al., Proc Natl Acad Sci USA 95: 446-471, 1998; Hallgren et al., Biochemistry 41(50): 15045-15055, 2002; and, Berkner et al., Proc Natl Acad Sci USA 89: 6242-6246, 1992).

For the purposes of this invention, the ratio of expression of the two proteins is determined indirectly via mRNA transcript level (e.g., by Taqman analysis).

In one embodiment the protein which requires gamma carboxylation is a vitamin K dependent coagulation factor. In a further embodiment, the protein which requires gamma-carboxylation is preferably selected from the group consisting of: prothrombin, coagulation factor II, coagulation FII, coagulation factor VII, coagulation FVII, coagulation factor IX, coagulation FIX, coagulation factor X, coagulation FX, Protein C, Protein S, Protein Z, Bone Gla protein, Matrix Gla protein, Growth arrest-specific protein 6 and Acanthophiinae FXa-like protein.

In one particular embodiment, the protein which requires gamma-carboxylation is Factor IX. In another particular embodiment, the protein which requires gamma-carboxylation is prothrombin. In another embodiment, the protein which requires gamma-carboxylation is Factor X.

The present invention has general application to proteins that require carboxylation from any source. However, if the expressed protein is to be used for human therapeutic purposes, human proteins are particularly preferred.

In one embodiment the γ-glutamyl carboxylase is of mouse, rat, bovine or conus snail origin. In another embodiment, the γ-glutamyl carboxylase is a human protein.

According to a further aspect of the invention there is provided a method for producing gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-carboxylated protein.

According to a further aspect of the invention there is provided a method for production of a gamma-carboxylated protein in a mammalian cell line, comprising the step of co-expressing with said protein requiring gamma-carboxylation in the mammalian cell line a γ-glutamyl carboxylase, wherein the amount of expressed protein requiring gamma-carboxylation is at least 10-fold greater than the amount of expressed γ-glutamyl carboxylase; and (ii) isolating gamma-carboxylated protein.

A method for producing a gamma-carboxylated protein comprising:

a) genetic modification of a eukaryotic cell to introduce a first polynucleotide encoding a protein that requires carboxylation and accompanying expression control sequences and a second polynucleotide encoding a γ-glutamyl carboxylase and accompanying expression control sequences to produce a eukaryotic host cell capable of co-expression of the protein that requires carboxylation and a γ-glutamyl carboxylase proteins in a ratio of at least 10:1;

b) cultivating the cell in suitable culture medium under conditions which allow the first and second polynucleotide sequences to be expressed; and c) isolation of the carboxylated protein from the medium or host cells.

Expression vectors usually include an origin of replication, a promoter, a translation initiation site, optionally a signal peptide, a polyadenylation site, and a transcription termination site. These vectors also usually contain one or more antibiotic resistance marker gene(s) for selection. Suitable expression vectors may be plasmids, cosmids or viruses such as phage or retroviruses. The coding sequence of the polypeptide is placed under the control of an appropriate promoter (i.e., HSV, CMV, TK, RSV, SV40 etc), control elements and transcription terminator (these are the associated expression control sequences) so that the nucleic acid sequence encoding the polypeptide is transcribed into RNA in the host cell transformed or transfected by the expression vector construct. The coding sequence may or may not contain a signal peptide or leader sequence for secretion of the polypeptide out of the host cell. Preferred vectors will usually comprise at least one multiple cloning site. In certain embodiments there will be a cloning site or multiple cloning site situated between the promoter and gene to be expressed. Such cloning sites can be used to create N-terminal fusion proteins by cloning a second nucleic acid sequence into the cloning site so that it is contiguous and in-frame with the gene sequence. In other embodiments there may be a cloning site or multiple cloning site situated immediately downstream of the gene to facilitate the creation of C-terminal fusions in a similar fashion to that for N-terminal fusions described above.

The host cell can be genetically modified (have extra nucleic acids introduced) by numerous methods, well known to a person skilled in the art, such as transfection, transformation and electroporation.

The invention also extends to purified gamma carboxylated protein produced by the methods of the present invention and their use in coagulant therapy.

According to yet another aspect of the invention there is provided a method of promoting increased or decreased coagulation in a subject comprising administering a pharmacologically effective amount of an isolated gamma-carboxylated protein obtained by the above-described methods to a patient in need thereof.

According to a further aspect of the invention there is provided a method of producing a pharmaceutical composition suitable for inducing blood clotting, comprising purifying active carboxylated protein expressed from a host cell adapted to express a protein requiring gamma-carboxylation and γ-glutamyl carboxylase in a ratio of at least 10:1 and admixing the purified carboxylated protein with one or more pharmaceutically acceptable carriers or excipients.

Protein-based therapeutics are usually stored frozen, refrigerated, at room temperature, and/or or in a freeze-dried state.

The compositions of the invention may be obtained by conventional procedures using conventional pharmaceutical excipients, well known in the art, but will most likely be in a form suitable for injection, either parenterally or directly into the wound site.

Aqueous suspensions generally contain the active ingredient in finely powdered form together with one or more suspending agents, such as sodium carboxymethylcellulose, methyl-cellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Powders suitable for preparation of an aqueous preparation for injection, by the addition of a suitable diluent, generally contain the active ingredient together with suitable carriers and excipients, suspending agent and one or more stabilisers or preservatives. The diluent may contain other suitable excipients, such as preservatives, tonicity modifiers and stabilizers.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate.

The pharmaceutical compositions of the invention may also be in the form of a sterile solution or suspension in a non-toxic parenterally acceptable diluent or solvent, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

For further information on Formulation the reader is referred to Chapter 25.2 in Volume 5 of Comprehensive Medicinal Chemistry (Corwin Hansch; Chairman of Editorial Board), Pergamon Press 1990; or, Volume 99 of Drugs and the pharmaceutical sciences; Protein formulation and delivery (Eugen J. McNally, executive editor), Marcel Dekker Inc 2000.

The amount of active ingredient that is combined with one or more excipients to produce a single dosage form will necessarily vary depending upon the host treated and the particular route of administration. For example, a formulation intended for injection to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of the active ingredient. Proteinaceous therapeutics are usually stored frozen or freeze-dried. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound will naturally vary according to the nature and severity of the conditions, the age and sex of the animal or patient and the route of administration, according to well known principles of medicine. In using a compound for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

The invention will be further described by the following non-limiting examples:

The practice of the present invention will employ, unless otherwise indicated, conventional methods of molecular biology and recombinant DNA techniques within the skill of the art. Such techniques are explained fully in the literature. See, e.g., Sambrook et al., eds., Molecular Cloning: A Laboratory Manual (3$^{rd}$ ed.) Cold Spring Harbor Laboratory Press, Cold Spring Harbor, N.Y. (2001); Ausubel et al., eds., Current Protocols in Molecular Biology, John Wiley & Sons, New York, N.Y. (2002); Glover & Hames, eds., DNA Cloning 3: A Practical Approach, Vols. I, II, & III, IRL Press, Oxford (1995); Colowick & Kaplan, eds., Methods in Enzymology, Academic Press; Weir et al., eds., Handbook of Experimental Immunology, 5$^{th}$ ed., Blackwell Scientific Publications, Ltd., Edinburgh, (1997).

Example 1

Amplification of cDNA Encoding Human FII (hPT) and Human GGCX

Human liver mRNA was purchased from Clontech and cDNA synthesis was performed using the Superscript system from Invitrogen. The obtained cDNA was used as template for amplification of human FII using:

```
primer PTF0                           (SEQ ID NO: 3)
5'-ATTCCTCAGTGACCCAGGAGCTGACA-3',
and

primer PTEXT                          (SEQ ID NO: 4).
5'-CTACTCTCCAAACTGATCAATGACCTTCTGTATCCACTTCTT-3',
```

Human GGCX was Amplified Using

```
primer hglx5,
5'-TCCGCAGAGCAATGGCGGTGTCT-3',    (SEQ ID NO: 5)
and

hglx3,
5'-CCAACATCTGGCCCCTTCAGAACT-3',   (SEQ ID NO: 6).
```

Figure 1B:
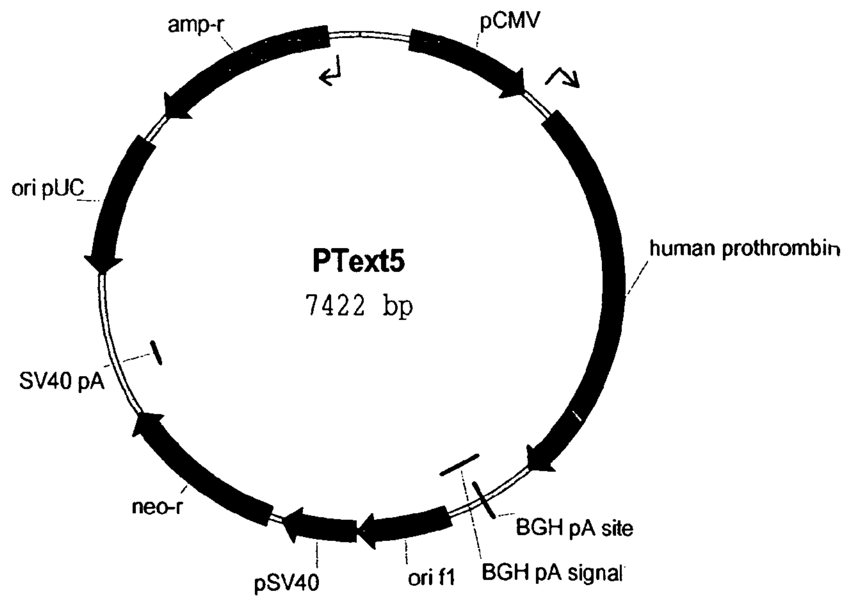
FIG. 1*b* represents a plasmid map of Ptext5 (prothrombin) expression vector.

The FII-encoding PCR product was cloned directly into the TA-TOPO treated vector pCDNA3.1V5/His (Invitrogen). Selection of a clone with hFII cDNA inserted in the correct direction gave the Ptext5 control construct (FIG. 1*b*). GGCX encoding cDNA under the control of the SV40 promoter was obtained by transfer of the GGCX encoding fragment from pCDNA3.1V5/His TA-TOPO to the pZeoSV2+ vector (Invitrogen), using restriction enzymes BamH1 and NotI. The EcoRV-NotI restriction sites downstream of the GGCX insert were removed. A blunted ClaI-BclI fragment from the resulting pZeoSV2-GGCX plasmid (containing the SV40 promoter and the GGCX containing insert, but not the polyadenylation site and polyadenylation signal downstream of the GGCX encoding sequence) was then cloned into the blunted DraIII restriction site of pCDNA3.1+(Invitrogen). A clone with the pSV40-GGCX fragment inserted in tandem (same transcriptional direction) relative to the CMV promoter was selected and a blunted KpnI-NotI FII encoding fragment from Ptext5 was cloned into the EcoRV site to obtain the PN32 construct (FIG. 1*a*). The DNA sequences of PN32 and Ptext5 are as in Appendix 2. All cloning methods were according to standard methods and/or manufacturers' recommended procedures.

The PN32 construct contains the following key features:

Human cytomegalovirus (hCMV) immediate-early promoter controlling transcription of human prothrombin cDNA followed by the Bovine Growth Hormone (BGH) polyadenylation signal for efficient transcription termination and polyadenylation of mRNA.

SV40 early promoter controlling transcription of human γ-carboxylase cDNA (GGCX) without apparent polyadenylation site or signal.

Other features are as shown in FIG. 1*a*).

For comparison the PText5 construct without GGCX was used (FIG. 1*b*). PTEXT5 nucleotide sequence is shown in SEQ ID NO: 1. PN32 nucleotide sequence is shown in SEQ ID NO: 2.

Prothrombin Producing Cell Lines Obtained

The two constructs in FIG. 1 were transfected into CHO-S cells (Invitrogen). Stable transfectants were selected and screened for highly productive clones using a commercially available assay for prothrombin activity (Chromogenix). In this assay the prothrombin containing samples were first treated with snake venom toxin (Ecarin—available from Sigma) to generate thrombin. Thrombin activity was then assayed by addition of a chromogenic substrate (S-2238)—which generates colour when processed by thrombin. Transfection and selection of clones were done in parallel with both constructs. Cell culturing was done in DMEM medium containing 9% heat inactivated fetal bovine serum. Clones obtained were then adapted to growth in animal component free medium. The best producing clone obtained was from transfection with PN32 (FII+GGCX), which yielded up to 400 mg/L human recombinant prothrombin when grown in animal component free chemically defined medium (far in excess of any published levels). Recombinantly produced rhFII was purified (according to the method disclosed in Josic et al., Journal of Chromatography B, 790: 183-197, 2003), and fractionated by ion-exchange chromatography using a Q-Sepharose column according to standard techniques, to obtain pure fully-carboxylated rhFII. Of fermentor produced rhFII up to 78 mg/L was fully-carboxylated and had the same biological activity as prothrombin purified from human plasma. Carboxylation was analysed by N-terminal sequencing of the protein and by prothrombinase assay (Mao et al. JBC, 273: 30086-30091, 1998). Thrombin generation was triggered in human platelet-poor plasma by the addition of tissue factor, and the endogenous thrombin potential was measured essentially as described by Stig et al., (Blood Coagulation and Fibrinolysis, 14: 457-462, 2003).

The best clone obtained with the PText5 construct gave a productivity of up to 10 mg/L in animal component free chemically defined medium, which is in the same range reported in the literature. The share of fully-carboxylated prothrombin obtained from the PText5 clone was estimated at around 50%. The final recovery of fully active rhFII was thus at least ten times higher using the PN32 construct containing a low expression level arrangement of the γ-carboxylase. For each of the constructs several clones with similar expression levels were identified.

Example 2

Measurement of ggcx Activity in CHO Cell Lines

Two rhFII producing CHO-S cell lines, obtained by transfection with the PN32 construct (co-expression of human GGCX) and PTEXT5 (no co-expression of GGCX), respectively, were grown in spinner bottles using protein free medium supplemented with 5 μg/ml vitamin K. One tenth of the growth medium was replaced daily. Cells were harvested after 7 days of culture and microsomes were prepared as described by Berkner et al., (Proc Natl Acad Sci USA 89: 6242-6246 1992). Human recombinant FII was purified from the culture supernate of the harvested cells. GGCX activity was measured as described by Berkner and Pudota (Proc Natl Acad Sci USA 95: 446-471 1998; and, Lingenfelter and Berkner (Biochemistry 35: 8234-8243, 1996). Our measurements showed that the GGCX activity is 1.5 times higher in the human GGCX co-expressing CHO cell line compared to the CHO cell line expressing only rhFII, using the same growth conditions.

Example 3

Real Time Reverse Transcription Polymerase Chain Reaction (RT-PCR) analysis of mRNA expression of γ-Carboxylase and Prothrombin in CHO-S Cell Lines Two CHO-S cell lines obtained by stable transfection with the PN32 (FII+GGCX) and Ptext5 (only FII) constructs respectively, were cultured in spinner bottles using protein free medium supplemented with vitamin K. Culture samples were withdrawn after 4, 5 and 6 days of culture to cover the estimated peak levels in mRNA production. RNA was isolated with Trizol™ according to the protocol supplied by the vendor, Invitrogen. The isolated RNA was DNaseI treated with the kit DNA-free™ from Ambion. cDNA synthesis was carried out using random hexamer primers and kit contents from Superscript™First-Strand Synthesis System for RT-PCR, Invitrogen.

Primers and Vic-labeled probes for Real-Time RT-PCR were selected using the software Primer Express™, Applied Biosystems.

Human γ-Carboxylase Oligonucleotides

```
5' ACACCTCTGGTTCAGACCTTTCTT 3'     Forward primer (SEQ ID NO: 7)
5' AATCGCTCATGGAAAGGAGTATTT 3'     Reverse primer (SEQ ID NO: 8)
5' CAACAAAGGCTCCAGGAGATTGAACGC 3'  Probe (SEQ ID NO: 9)
```

Amplicon Length 86 bp

Human Prothrombin Oligonucleotides

```
5' TGGAGGACAAAACCGAAAGAGA 3'    Forward primer (SEQ ID NO: 10)
5' CATCCGAGCCCTCCACAA 3'        Reverse primer (SEQ ID NO: 11)
5' CTCCTGGAATCCTACATCGACGGGC 3' Probe (SEQ ID NO: 12)
```

Amplicon Length 69 bp

Primers were manufactured by Operon/Qiagen and the probes were ordered from Applied Biosystems. Rodent GAPDH control primers and probe were also used (Applied Biosystems; ABI # 4308318 TaqMan® Rodent GAPDH Control Reagents Protocol)-Amplicon length 177 bp. The Real-Time RT-PCR reactions were performed on the ABI Prism™ 7700 Sequence detector, Applied Biosystems. The expected length of the amplified PCR products was confirmed on agarose gels. Dilution series to investigate the efficiency of the PCR reactions were carried out for all three genes. Expression levels of γ-Carboxylase and Prothrombin are presented relative to the expression of the control gene, rodent GAPDH.

| | CHO-S PText5 day 4 | CHO-S PText5 day5 | CHO-S PText5 day6 | CHO-S PN32 day 4 | CHO-S PN32 day 5 | CHO-S PN32 day 6 |
|---|---|---|---|---|---|---|
| | | | Prothrombin | | | |
| 2^-delta Ct | 0.008014 | 0.076239 | 0.066677 | 0.204948 | 0.322343 | 0.364334 |
| | | | γ-Carboxylase | | | |
| 2^-delta Ct | 3.39E−07 | 0 | 0 | 0.000277 | 0.00159 | 0.001568 |

From the relative expression levels the of rhFII:GGCX detected, ratios of approximately 74-232:1 were calculated depending on day of sample collection. For the cell line transfected with PN32, co-expression rhFII and GGCX, the number of transcript per cell were calculated to be approximately 8 for the GGCX mRNA and approximately 2000 for the rhFII mRNA, thus giving a rhFII:GGCX ratio of approximately 250:1. The GAPDH control mRNA transcripts/cell was for the same sample approximately 4000.

Example 4

Production of Human FII

Figure 2:
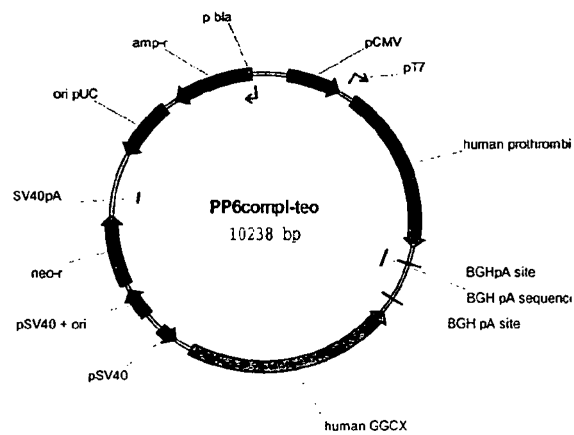
FIG. 2 represents a plasmid map of PP6 (prothrombin+GGCX) co-expression vector.

The human FII and GGCX cDNA cloned in Example 1 were inserted into pCDNA3.1 similarly as in Ex.1. In order to give higher GGCX levels, the polyadenylation signal from pZeoSV2+ was included in the pSV40-GGCX-pA fragment cloned into the blunted DraIII site of pCDNA3.1. A clone with the GGCX-containing fragment in the reverse order compared to Ex. 1 was selected. Cloning of the FII fragment was then done the same way as in Ex 1. The final construct PP6 is shown in FIG. 2 and the PP6 nucleotide sequence is shown in SEQ ID NO: 13.

Two prothrombin producing cell lines, B2F4 and H3B10 were obtained by transfecting CHO-S as described in Ex 1. Prothrombin from these two cell lines was purified and characterized as in Ex 1. Cultures of B2F4 gave productivities ranging from 30-70 mg/L and the share of fully carboxylated from 55-87% (the more rhFII the less fully carboxylated). Addition of butyrate gave a somewhat higher productivity but decreased the share of fully carboxylated rhFII and was not considered to be beneficial. H3B10 is slow-growing and gave a productivity of about 50 mg/L, which was high relative to the amount of cells in the culture, and the share of fully carboxylated rhFII was around 60%. Compared to the cell line obtained in example 1, less fully carboxylated rhFII was produced using the PP6 construct for a CHO cell line. The production of fully active recombinant prothrombin is still, however, far above earlier published levels.

Example 5

Real Time RT-PCR Analyses of the Expression of γ-Carboxylase and Prothrombin in CHO-S Cell Lines by Measuring Amount of mRNA The B2F4 and H3B10 cell lines from example 4 were analysed by real-time PCR analyses by the same method and the same primers as in Ex 3. Culture samples of 10 ml were collected at peak productivity in order to be equivalent to samples in Ex 3. For clone H3B10 samples were from day 10 due to the slow growth of this clone, and for clone B2F4 samples were from day 6.

TABLE 4

Results from Real time RT-PCR analyses of prothrombin producing cell lines co-expressing GGCX. Two independent 100 ml spinner cultures for each B2F4 and H3B10 were sampled for Real-Time RT-PCR analyses.

| Transcript | Total # cells | Resulting amount of total RNA | Total RNA used for RT-PCR | Amount mRNA in RT-PCR | Number of cells in RT-PCR | Ct | Copies mRNA | Copies mRNA/cell |
|---|---|---|---|---|---|---|---|---|
| P1E2* Day 6 | | | | | | | | |
| PT | 2.00E+07 | 2.39E−04 | 1.25E−08 | 2.50E−09 | 1.05E+03 | 19 | 2.10E+06 | 2005 |
| GGCX | 2.00E+07 | 2.39E−04 | 1.25E−08 | 2.50E−09 | 1.05E+03 | 27 | 8.19E+03 | 8 |
| GAPDH | 2.00E+07 | 2.39E−04 | 1.25E−08 | 2.50E−09 | 1.05E+03 | 18 | 4.19E+06 | 4010 |
| B2F4-1 Day 6 | | | | | | | | |
| PT | 1.30E+07 | 2.20E−04 | 1.25E−08 | 2.50E−09 | 7.39E+02 | 19.2 | 1.83E+06 | 2472 |
| GGCX | 1.30E+07 | 2.20E−04 | 1.25E−08 | 2.50E−09 | 7.39E+02 | 24.1 | 6.11E+04 | 83 |
| GAPDH | 1.30E+07 | 2.20E−04 | 1.25E−08 | 2.50E−09 | 7.39E+02 | 19.8 | 1.20E+06 | 1631 |
| B2F4-2 Day 6 | | | | | | | | |
| PT | 1.10E+07 | 1.40E−04 | 1.25E−08 | 2.50E−09 | 9.82E+02 | 19.2 | 1.83E+06 | 1859 |
| GGCX | 1.10E+07 | 1.40E−04 | 1.25E−08 | 2.50E−09 | 9.82E+02 | 24.1 | 6.11E+04 | 62 |
| GAPDH | 1.10E+07 | 1.40E−04 | 1.25E−08 | 2.50E−09 | 9.82E+02 | 19 | 2.10E+06 | 2135 |
| H3B10-1 Day 10 | | | | | | | | |
| PT | 1.10E+07 | 2.90E−04 | 1.25E−08 | 2.50E−09 | 4.74E+02 | 17.77 | 4.92E+06 | 10375 |
| GGCX | 1.10E+07 | 2.90E−04 | 1.25E−08 | 2.50E−09 | 4.74E+02 | 23.4 | 9.93E+04 | 210 |
| GAPDH | 1.10E+07 | 2.90E−04 | 1.25E−08 | 2.50E−09 | 4.74E+02 | 17.96 | 4.31E+06 | 9095 |
| H3B10-2 Day 10 | | | | | | | | |
| PT | 8.90E+06 | 3.10E−04 | 1.25E−08 | 2.50E−09 | 3.59E+02 | 19.2 | 1.83E+06 | 5087 |
| GGCX | 8.90E+06 | 3.10E−04 | 1.25E−08 | 2.50E−09 | 3.59E+02 | 25.3 | 2.66E+04 | 74 |
| GAPDH | 8.90E+06 | 3.10E−04 | 1.25E−08 | 2.50E−09 | 3.59E+02 | 18.9 | 2.25E+06 | 6263 |

*P1E2 data from example 3 for comparison.

The calculated ratio rhFII mRNA: GGCX mRNA was approximately 30:1 for clone H3B10, approximately 50:1 for clone B2F4 and approximately 250:1 for clone P1E2.

Example 6

Production of Human Coagulation Factor IX (FIX)

Human coagulation factor IX cDNA was amplified from human Gene pool liver cDNA purchased from Invitrogen. Oligonucleotide primers were for

```
the 5'-end; F9f.ampl.:
5'-CACCATGCAGCGCGTGAACATGAT-3',   (SEQ ID NO: 16)
and

the 3'-end; F9r.ampl.:
5'-CCTTGGAAATCCATCTTTCATTA-3'.    (SEQ ID NO: 17)
```

Figure 3A:
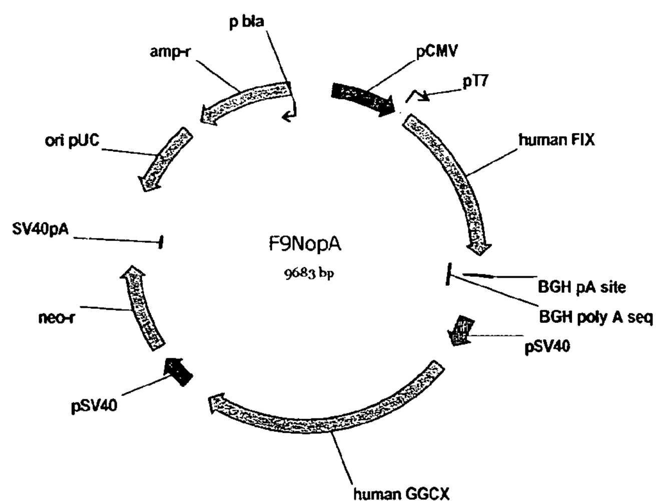
FIG. 3*a* represents a plasmid map of F9NopA (factor IX+GGCX) co-expression vector
Figure 3B:
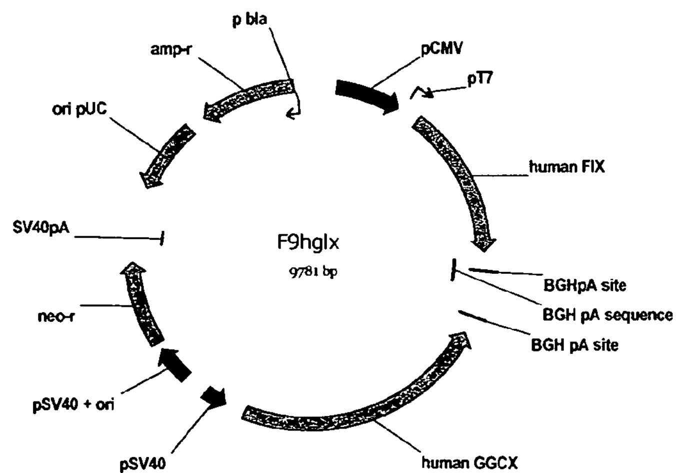
FIG. 3*b* represents a plasmid map of F9hglx (factor IX+GGCX) co-expression vector.

Cloning of the correct sequence was confirmed by DNA sequencing. The human FIX fragment was PCR amplified using Pfx polymerase (Invitrogen) and the cloning primers to produce a blunt ended fragment. The blunt-ended fragment was phosphorylated using T4 polynucleotide kinase, and cloned into the EcoRV digested and de-phosphorylated pCDNA-GGCX vectors from Ex. 1 and Ex 4. In this way constructs for co-expression of human FIX and GGCX analogous to the co-expression constructs used for production of human prothrombin (Ex.1 and 4) were obtained. Cloning of the correct sequences was confirmed by DNA sequencing and transient expression in COS-7 cells. The vector construct F9NopA can be seen in FIG. 3*a* and the vector construct F9hglx is shown in FIG. 3*b*. The difference between the vectors F9NopA and F9hglx is the transcription direction of the GGCX gene. The F9NopA nucleotide sequence is shown in SEQ ID NO: 14 and the F9hglx nucleotide sequence is shown in SEQ ID NO: 15.

Establishment of Cell Lines Producing rhFIX

The rhFIX constructs were transfected to CHO-S cells using the procedure described in Ex1. For each FIX construct approximately 3000 clones were screened for rhFIX expression by ELISA of cell supernates. Antibodies used were from Haemathology Technology Inc. and DakoCytomation. Clones were selected and adapted to growth in protein free chemically defined CHO medium. Cells were grown either in T-flasks at 37° C. or in spinner bottles at 32-37° C. $CO_2$ concentration was 5% for both types of cultures. The rhFIX produced was purified to homogeneity by Q-Sepharose anion exchange chromathography at pH 7.0. Recombinant hFIX activity was determined by Clotting assay using FIX deficient plasma (Precision Biologic). The best producing rhFIX clone obtained was N4D5, which was obtained using the F9NopA construct, produced up to 4 μg/ml active rhFIX grown in protein free chemically defined medium in T-flask. Grown in spinner bottle the same clone produced up to 7.1 μg/ml rhFIX. The overall productivity, also including incompletely carboxylated, non-active rhFIX, was estimated by Western blotting to be at least 30 μg/ml. The best producing clone obtained with the rhFIX construct F9hglx was P1G9 that produced 0.7 (T-flask)-1.3 (spinner) μg/ml rhFIX under similar conditions. The results indicate that rhFIX productivity improved by co-expression of GGCX at a low level using the F9NopA construct, but that co-expression of GGCX using construct F9hglx, was less beneficial. It was also noted that the F9NopA construct, giving rise to the N4D5 clone, generally gave higher ELISA signals than the F9hglx construct, giving rise to the P1G9 clone, in simultaneous screens for productivity during the cell line development procedure.

The productivity of the N4D5 cell line is approximately 4-6 better than previously published levels obtained under comparable conditions, wherein IC4, IG8, r-FIX BHK and r-FIX 293 is the name of the clones mentioned in the references (Table 5).

TABLE 5

Comparison of productivity from human FIX producing cell lines.

| Cell line/construct | Amount of active rhFIX produced T-flask (μg/ml) | Amount of active rhFIX produced Spinner (μg/ml) | Total productivity (μg/ml) | Reference |
|---|---|---|---|---|
| N4D5/F9NopA CHO, low GGXC co-expr. | 4 | 7.1 | >30 | Example 6 |
| P1G9/F9hglx CHO, medium GGCX co-expr. | 0.7 | 1.3 | nd | Example 6 |
| IC4 CHO, HA (control) co-expr. | 0.9 | nd | 30 | Rehemtulla 1993. |
| IC4 CHO. High GGCX co-expr. | 1 | nd | 29 | Rehemtulla 1993. |
| IC4 | 0.9 | nd | 20 | U.S. Pat. No. 5,460,950 |
| 1G8 CHO | 1.5 | nd | 43 | Kaufman, RJ et al 1986 JBC 261: 9622-9628 |
| r-FIX BHK | 0.004/24 h | nd | 0.004/24 h | Hallgren 2002 |
| r-FIX 293 | 0.004/24 h | nd | 0.004/24 h | Hallgren 2002 |

Example 7

Real-Time RT-PCR Analyses of the Expression of γ-Carboxylase and Factor IX in CHO-S Cell Lines by Measuring Amount of mRNA Recombinant hFIX-producing clones were grown in spinner bottles at 32-37° C., in 100 ml protein free chemically defined medium supplemented with Vitamin K. Samples of 5-10 ml were collected at peak rhFIX concentration and analysed for content of human FIX and GGCX transcripts, as well as transcripts of the GAPDH control (house-keeping) gene. Procedure was as in example 3. Primers for rhFIX were as follows:

Human Factor IX Primers

```
5' AATAGTGCTGATAACAAGGTGGTTTG 3'       Forward primer (SEQ ID NO: 18)

5' CACTGCTGGTTCACAGGACTTCT 3'          Reverse primer (SEQ ID NO: 19)

5' TCCTGTACTGAGGGATATCGACTTGCAGAAAAC 3' Probe (SEQ ID NO: 20)
```

Amplicon Length 84 bp

Messenger RNA levels were found to peak at different days depending on culture temperature and culture inoculum size. Peak levels of mRNA were found to correspond well with peak concentration of rhFIX in the culture medium.

TABLE 6

Results from Real-Time RT-PCR analyses of rhFIX-producing clones.

| Cell line-batch | Day of culture | 2^-delta Ct FIX | 2^-delta Ct GGCX | mRNA ratio FIX:GGCX |
|---|---|---|---|---|
| N4D5-100 | 11 | 0.255253 | 0.005461 | 47:1 |
| N4D5-2 | 14 | 0.264866 | 0.006201 | 43:1 |
| P1G9-A | 6 | 0.022982 | 0.005601 | 4:1 |
| P1G9-B | 8 | 0.04181 | 0.007687 | 5:1 |

From Real-Time RT-PCR analyses we also found that, although 2^-delta Ct-values varied with culture time and conditions, the FIX:GGCX mRNA ratios were approximately the same for each clone. For the best rhFIX-producing clone N4D5 the ratio was approximately 45:1. Analyses of another clone, P1G9, gave a lower ratio of approximately 4.5:1. The P1G9 clone produced only 20% of the amount rhFIX produced by N4D5.

The invention claimed is:

1. A method for producing a protein, the method comprising:

(a) providing a recombinant host cell containing a first nucleic acid comprising a first promoter operably linked to a nucleotide sequence encoding a protein requiring gamma-carboxylation and a second heterologous nucleic acid comprising a second promoter operably linked to a nucleotide sequence encoding a γ-glutamyl carboxylase, wherein the first promoter is stronger than the second promoter;

(b) culturing the cell under conditions suitable for expressing both nucleic acids, wherein the protein requiring gamma-carboxylation and the γ-glutamyl carboxylase are expressed in a ratio of at least 10:1 and the protein requiring gamma-carboxylation is carboxylated in the cell, thereby producing a gamma-carboxylated protein;

(c) isolating the gamma-carboxylated protein or an activated form thereof; and (d) preparing a pharmaceutical composition comprising the isolated gamma-carboxylated protein or an activated form thereof.

2. The method of claim 1, wherein the first and second nucleic acids are within a single expression vector.

3. The method of claim 1, wherein the first promoter is selected from the group consisting of human cytomegalovirus (hCMV) immediate-early promoter, human elongation factor-1α subunit gene (pEF-1α) promoter, Rous sarcoma virus promoter (pRSV) and human ubiquitin promoter (pUbC).

4. The method of claim 1, wherein the second promoter is selected from the group consisting of SV40 immediate early promoter, minimized FIX promoter and HSV Thymidine kinase promoter.

5. The method of claim 3, wherein the second promoter is selected from the group consisting of SV40 immediate early promoter, minimized FIX promoter and HSV Thymidine kinase promoter.

6. The method of claim 1, wherein the first promoter is human cytomegalovirus (hCMV) immediate-early promoter and the second promoter is SV40 immediate early promoter.

7. The method of claim 1, wherein the protein requiring gamma-carboxylation and the γ-glutamyl carboxylase are expressed in a ratio between 10:1 and 500:1.

8. The method of claim 1, wherein the protein requiring gamma-carboxylation is a human protein.

9. The method of claim 1, wherein the γ-glutamyl carboxylase is a human protein.

10. The method of claim 1, wherein the protein requiring gamma-carboxylation is coagulation factor VII, coagulation factor IX, coagulation factor II (prothrombin), coagulation factor X, Protein C, Protein S, Protein Z, Bone Gla protein, Matrix Gla protein, Growth arrest-specific protein 6 or Acanthophiinae FXa-like protein.

11. The method of claim 1, wherein the protein requiring gamma-carboxylation is a vitamin K dependent coagulation factor.

12. The method of claim 1, wherein the protein requiring gamma-carboxylation is Factor IX.

13. The method of claim 1, wherein the protein requiring gamma-carboxylation is Factor X.

14. The method of claim 1, wherein the protein requiring gamma-carboxylation is Factor II (prothrombin).

15. The method of claim 1, wherein the cell is a mammalian cell.

16. The method of claim 1, wherein the cell is a yeast cell or an insect cell.

17. The method of claim 1, wherein the cell is a CHO cell, a HEK293 cell, a NSO cell, a Per C.6 cell, a BHK cell, or a COS cell.

18. A method for producing a protein, the method comprising:

(a) providing a genetically modified cell that expresses a first DNA encoding a protein requiring gamma-carboxylation and a second DNA encoding a γ-glutamyl carboxylase;

(b) culturing the cell under conditions suitable for expressing both DNAs, wherein the protein requiring gamma-carboxylation is expressed and gamma-carboxylated in the cell, thereby producing a gamma-carboxylated protein; and (c) isolating the gamma-carboxylated protein or an activated form thereof, wherein the level of γ-glutamyl carboxylase mRNA expressed in the genetically modified cell is (i) higher than the level of γ-glutamyl carboxylase mRNA expressed under identical conditions in a second cell identical to the genetically modified cell except that it has not been genetically modified, and (ii) less than or equal to 10% of the level of mRNA encoding the protein requiring gamma-carboxylation expressed in the genetically modified cell.

19. The method of claim 18, wherein the second DNA is an endogenous coding sequence under the control of a heterologous regulatory sequence introduced into the genetically modified cell, or an ancestor thereof, by recombinant technology.

20. The method of claim 18, wherein the second DNA was introduced into the genetically modified cell, or an ancestor thereof, by recombinant technology.

21. The method of claim 18, wherein the first DNA is under the control of a first promoter, the second DNA is under the control of a second promoter, and the first promoter is stronger than the second promoter.

22. The method of claim 21, wherein the first promoter is selected from the group consisting of human cytomegalovirus (hCMV) immediate-early promoter, human elongation factor-1α subunit gene (pEF-1α) promoter, Rous sarcoma virus promoter (pRSV) and human ubiquitin promoter (pUbC).

23. The method of claim 21, wherein the second promoter is selected from the group consisting of SV40 immediate early promoter, minimized FIX promoter and HSV Thymidine kinase promoter.

24. The method of claim 22, wherein the second promoter is selected from the group consisting of SV40 immediate early promoter, minimized FIX promoter and HSV Thymidine kinase promoter.

25. The method of claim 18, wherein the protein requiring gamma-carboxylation is coagulation factor VII, coagulation factor IX, coagulation factor II (prothrombin), coagulation factor X, Protein C, Protein S, Protein Z, Bone Gla protein, Matrix Gla protein, Growth arrest-specific protein 6 or Acanthophiinae FXa-like protein.

26. The method of claim 18, wherein the protein requiring gamma-carboxylation is a vitamin K dependent coagulation factor.

27. The method of claim 18, wherein the protein requiring gamma-carboxylation is Factor IX.

28. The method of claim 18, wherein the protein requiring gamma-carboxylation is Factor X.

29. The method of claim 18, wherein the protein requiring gamma-carboxylation is Factor II (prothrombin).

30. The method of claim 18, wherein the cell is a mammalian cell.

31. The method of claim 18, wherein the cell is a yeast cell or an insect cell.

32. The method of claim 18, wherein the cell is a CHO cell, a HEK293 cell, a NSO cell, a Per C.6 cell, a BHK cell, or a COS cell.

33. The method of claim 21, further comprising (d) preparing a pharmaceutical composition comprising the isolated gamma-carboxylated protein or an activated form thereof.

34. A method for producing a gamma-carboxylated protein, the method comprising:

(a) providing a cell containing a first DNA encoding a human protein requiring gamma-carboxylation and a second DNA encoding a γ-glutamyl carboxylase, wherein each of the first and second DNAs was introduced into the cell, or an ancestor of the cell, by recombinant technology;

(b) culturing the cell under conditions suitable for expressing both DNAs, wherein the protein requiring gamma-carboxylation is expressed and gamma-carboxylated in the cell, thereby producing a gamma-carboxylated protein; and (c) isolating the gamma-carboxylated protein, wherein the level of γ-glutamyl carboxylase mRNA expressed in the cell is less than or equal to 10% of the level of mRNA expressed from the first DNA.

35. The method of claim 34, wherein the first DNA is under the control of a first promoter, the second DNA is under the control of a second promoter, and the first promoter is stronger than the second promoter.

36. The method of claim 35, wherein the first promoter is selected from the group consisting of human cytomegalovirus (hCMV) immediate-early promoter, human elongation factor-1α subunit gene (pEF-1α) promoter, Rous sarcoma virus promoter (pRSV) and human ubiquitin promoter (pUbC).

37. The method of claim 35, wherein the second promoter is selected from the group consisting of SV40 immediate early promoter, minimized FIX promoter and HSV Thymidine kinase promoter.

38. The method of claim 34, wherein the second promoter is selected from the group consisting of SV40 immediate early promoter, minimized FIX promoter and HSV Thymidine kinase promoter.

39. The method of claim 34, wherein the protein requiring gamma-carboxylation is coagulation factor VII, coagulation factor IX, coagulation factor II (prothrombin), coagulation factor X, Protein C, Protein S, Protein Z, Bone Gla protein, Matrix Gla protein, Growth arrest-specific protein 6 or Acanthophiinae FXa-like protein.

40. The method of claim 34, wherein the cell is a mammalian cell.

41. The method of claim 34, wherein the cell is a yeast cell or an insect cell.

42. The method of claim 34, wherein the cell is a CHO cell, a HEK293 cell, a NSO cell, a Per C.6 cell, a BHK cell, or a COS cell.

43. The method of claim 34, further comprising (d) preparing a pharmaceutical composition comprising the isolated gamma-carboxylated protein or an activated form thereof.

44. The method of claim 18, wherein the protein requiring gamma-carboxylation and the γ-glutamyl carboxylase are expressed in a ratio between 10:1 and 500:1.

45. The method of claim 34, wherein the protein requiring gamma-carboxylation and the γ-glutamyl carboxylase are expressed in a ratio between 10:1 and 500:1.

46. The method of claim 1, wherein the protein requiring gamma-carboxylation is Factor VII.

47. The method of claim 18, wherein the protein requiring gamma-carboxylation is Factor VII.

48. The method of claim 34, wherein the protein requiring gamma-carboxylation is Factor VII.

49. The method of claim 34, wherein the protein requiring gamma-carboxylation is Factor IX.

50. The method of claim 34, wherein the protein requiring gamma-carboxylation is Factor X.

51. The method of claim 34, wherein the protein requiring gamma-carboxylation is Factor II (prothrombin).

52. The method of claim 1, wherein step (c) comprises isolating an activated form of Factor II, Factor VII, Factor IX, Factor X or Protein C.

53. The method of claim 18, wherein step (c) comprises isolating an activated form of Factor II, Factor VII, Factor IX, Factor X or Protein C.

54. The method of claim 34, wherein step (c) comprises isolating an activated form of Factor II, Factor VII, Factor IX, Factor X or Protein C.

55. The method of claim 18, further comprising:

(d) preparing a pharmaceutical composition comprising the isolated gamma-carboxylated protein or an activated form thereof.

56. The method of claim 27, further comprising:

(d) preparing a pharmaceutical composition comprising the isolated gamma-carboxylated protein or an activated form thereof.

57. The method of claim 28, further comprising:

(d) preparing a pharmaceutical composition comprising the isolated gamma-carboxylated protein or an activated form thereof.

58. The method of claim 29, further comprising:

(d) preparing a pharmaceutical composition comprising the isolated gamma-carboxylated protein or an activated form thereof.

59. The method of claim 1, wherein the protein requiring gamma-carboxylation is Protein C.

60. The method of claim 18, wherein the protein requiring gamma-carboxylation is Protein C.

61. The method of claim 60, further comprising:

(d) preparing a pharmaceutical composition comprising the isolated gamma-carboxylated protein or an activated form thereof.

62. The method of claim 34, wherein the protein requiring gamma-carboxylation is Protein C.

63. The method of claim 62, further comprising:

(d) preparing a pharmaceutical composition comprising the isolated gamma-carboxylated protein or an activated form thereof.

64. The method of claim 47, further comprising:

(d) preparing a pharmaceutical composition comprising the isolated gamma-carboxylated protein or an activated form thereof.

65. The method of claim 48, further comprising:

(d) preparing a pharmaceutical composition comprising the isolated gamma-carboxylated protein or an activated form thereof.

66. A method for producing a protein, the method comprising:

(a) providing a recombinant host cell containing a first nucleic acid comprising a first promoter operably linked to a nucleotide sequence encoding a protein requiring gamma-carboxylation and a second heterologous nucleic acid comprising a second promoter operably linked to a nucleotide sequence encoding a γ-glutamyl carboxylase, wherein the first promoter is stronger than the second promoter;

(b) culturing the cell under conditions suitable for expressing both nucleic acids, wherein the protein requiring gamma-carboxylation and the γ-glutamyl carboxylase are expressed in a ratio of at least 10:1 and the protein requiring gamma-carboxylation is carboxylated in the cell, thereby producing a gamma-carboxylated protein; and (c) isolating the gamma-carboxylated protein or an activated form thereof.

67. The method of claim 66, further comprising:

(d) preparing a pharmaceutical composition comprising the isolated gamma-carboxylated protein or an activated form thereof.

* * * * *

UNITED STATES PATENT AND TRADEMARK OFFICE

CERTIFICATE OF CORRECTION

PATENT NO. : 7,842,477 B2
APPLICATION NO. : 10/964888
DATED : November 30, 2010
INVENTOR(S) : Christel Fenge, Ann Lövgren and Anders Thelin It is certified that error appears in the above-identified patent and that said Letters Patent is hereby corrected as shown below:

In Column 70, line 2, in claim 17, delete “NSO” and insert -- NS0 --

In Column 71, line 4, in claim 32, delete “NSO” and insert -- NS0 --

In Column 71, line 41, in claim 38, delete “claim 34,” and insert -- claim 36, --

In Column 71, line 56, in claim 42, delete “NSO” and insert -- NS0 --

Signed and Sealed this
Fourteenth Day of June, 2011

David J. Kappos
*Director of the United States Patent and Trademark Office*

SEQUENCE LISTING

<160> NUMBER OF SEQ ID NOS: 15

<210> SEQ ID NO 1
<211> LENGTH: 7422
<212> TYPE: DNA
<213> ORGANISM: Artificial
<220> FEATURE:
<223> OTHER INFORMATION: Vector

<400> SEQUENCE: 1

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagcttggt accgagctcg gatccactag tccagtgtgg tggaattgcc cttattcctc    960

agtgacccag gagctgacac actatggcgc acgtccgagg cttgcagctg cctggctgcc   1020

tggccctggc tgccctgtgt agccttgtgc acagccagca tgtgttcctg gctcctcagc   1080

aagcacggtc gctgctccag cgggtccggc gagccaacac cttcttggag gaggtgcgca   1140

agggcaacct ggagcgagag tgcgtggagg agacgtgcag ctacgaggag gccttcgagg   1200

ctctggagtc ctccacggct acggatgtgt tctgggccaa gtacacagct tgtgagacag   1260

cgaggacgcc tcgagataag cttgctgcat gtctggaagg taactgtgct gagggtctgg   1320

gtacgaacta ccgagggcat gtgaacatca cccggtcagg cattgagtgc cagctatgga   1380

ggagtcgcta cccacataag cctgaaatca actccactac ccatcctggg gccgacctac   1440

aggagaattt ctgccgcaac cccgacagca gcaccacggg accctggtgc tacactacag   1500

accccaccgt gaggaggcag gaatgcagca tccctgtctg tggccaggat caagtcactg   1560

tagcgatgac tccacgctcc gaaggctcca gtgtgaatct gtcacctcca ttggagcagt   1620

gtgtccctga tcgggggcag cagtaccagg ggcgcctggc ggtgaccaca catgggctcc   1680

cctgcctggc ctgggccagc gcacaggcca aggccctgag caagcaccag gacttcaact   1740

cagctgtgca gctggtggag aacttctgcc gcaacccaga cggggatgag gagggcgtgt   1800

ggtgctatgt ggccgggaag cctggcgact ttgggtactg cgacctcaac tattgtgagg   1860

aggccgtgga ggaggagaca ggagatgggc tggatgagga ctcagacagg gccatcgaag   1920

ggcgtaccgc caccagtgag taccagactt tcttcaatcc gaggaccttt ggctcgggag   1980
```

-continued

```
aggcagactg tgggctgcga cctctgttcg agaagaagtc gctggaggac aaaaccgaaa   2040
gagagctcct ggaatcctac atcgacgggc gcattgtgga gggctcggat gcagagatcg   2100
gcatgtcacc ttggcaggtg atgcttttcc ggaagagtcc ccaggagctg ctgtgtgggg   2160
ccagcctcat cagtgaccgc tggtcctca ccgccgccca ctgcctcctg tacccgccct   2220
gggacaagaa cttcaccgag aatgaccttc tggtgcgcat tggcaagcac tcccgcacca   2280
ggtacgagcg aaacattgaa aagatatcca tgttggaaaa gatctacatc caccccaggt   2340
acaactggcg ggagaacctg gaccgggaca ttgccctgat gaagctgaag aagcctgttg   2400
ccttcagtga ctacattcac cctgtgtgtc tgcccgacag ggagacggca gccagcttgc   2460
tccaggctgg atacaagggg cgggtgacag gctggggcaa cctgaaggag acgtggacag   2520
ccaacgttgg taaggggcag cccagtgtcc tgcaggtggt gaacctgccc attgtggagc   2580
ggccggtctg caaggactcc acccggatcc gcatcactga caacatgttc tgtgctggtt   2640
acaagcctga tgaagggaaa cgaggggatg cctgtgaagg tgacagtggg ggaccctttg   2700
tcatgaagag cccctttaac aaccgctggt atcaaatggg catcgtctca tggggtgaag   2760
gctgtgaccg ggatgggaaa tatggcttct acacacatgt gttccgcctg aagaagtgga   2820
tacagaaggt cattgatcag tttggagagt agaagggcaa ttctgcagat atccagcaca   2880
gtggcggccg ctcgagtcta gagggcccgc ggttcgaagg taagcctatc cctaaccctc   2940
tcctcggtct cgattctacg cgtaccggtc atcatcacca tcaccattga gtttaaaccc   3000
gctgatcagc ctcgactgtg ccttctagtt gccagccatc tgttgtttgc ccctcccccg   3060
tgccttcctt gaccctggaa ggtgccactc ccactgtcct ttcctaataa aatgaggaaa   3120
ttgcatcgca ttgtctgagt aggtgtcatt ctattctggg gggtggggtg gggcaggaca   3180
gcaaggggga ggattgggaa gacaatagca ggcatgctgg ggatgcggtg ggctctatgg   3240
cttctgaggc ggaaagaacc agctggggct ctagggggta tccccacgcg ccctgtagcg   3300
gcgcattaag cgcggcgggt gtggtggtta cgcgcagcgt gaccgctaca cttgccagcg   3360
ccctagcgcc cgctcctttc gctttcttcc cttcctttct cgccacgttc gccggctttc   3420
cccgtcaagc tctaaatcgg ggcatccctt tagggttccg atttagtgct ttacggcacc   3480
tcgaccccaa aaaacttgat tagggtgatg gttcacgtag tgggccatcg ccctgataga   3540
cggtttttcg ccctttgacg ttggagtcca cgttctttaa tagtggactc ttgttccaaa   3600
ctggaacaac actcaaccct atctcggtct attcttttga tttataaggg attttgggga   3660
tttcggccta ttggttaaaa aatgagctga tttaacaaaa atttaacgcg aattaattct   3720
gtggaatgtg tgtcagttag ggtgtggaaa gtccccaggc tccccaggca ggcagaagta   3780
tgcaaagcat gcatctcaat tagtcagcaa ccaggtgtgg aaagtcccca ggctccccag   3840
caggcagaag tatgcaaagc atgcatctca attagtcagc aaccatagtc ccgcccctaa   3900
ctccgcccat cccgccccta actccgccca gttccgccca ttctccgccc catggctgac   3960
taattttttt tatttatgca gaggccgagg ccgcctctgc ctctgagcta ttccagaagt   4020
agtgaggagg cttttttgga ggcctaggct tttgcaaaaa gctcccggga gcttgtatat   4080
ccattttcgg atctgatcaa gagacaggat gaggatcgtt tcgcatgatt gaacaagatg   4140
gattgcacgc aggttctccg gccgcttggg tggagaggct attcggctat gactgggcac   4200
aacagacaat cggctgctct gatgccgccg tgttccggct gtcagcgcag gggcgcccgg   4260
ttctttttgt caagaccgac ctgtccggtg ccctgaatga actgcaggac gaggcagcgc   4320
```

-continued

```
ggctatcgtg gctggccacg acgggcgttc cttgcgcagc tgtgctcgac gttgtcactg   4380
aagcgggaag ggactggctg ctattgggcg aagtgccggg gcaggatctc ctgtcatctc   4440
accttgctcc tgccgagaaa gtatccatca tggctgatgc aatgcggcgg ctgcatacgc   4500
ttgatccggc tacctgccca ttcgaccacc aagcgaaaca tcgcatcgag cgagcacgta   4560
ctcggatgga agccggtctt gtcgatcagg atgatctgga cgaagagcat caggggctcg   4620
cgccagccga actgttcgcc aggctcaagg cgcgcatgcc cgacggcgag gatctcgtcg   4680
tgacccatgg cgatgcctgc ttgccgaata tcatggtgga aaatggccgc ttttctggat   4740
tcatcgactg tggccggctg ggtgtggcgg accgctatca ggacatagcg ttggctaccc   4800
gtgatattgc tgaagagctt ggcggcgaat gggctgaccg cttcctcgtg ctttacggta   4860
tcgccgctcc cgattcgcag cgcatcgcct tctatcgcct tcttgacgag ttcttctgag   4920
cgggactctg gggttcgcga aatgaccgac caagcgacgc ccaacctgcc atcacgagat   4980
ttcgattcca ccgccgcctt ctatgaaagg ttgggcttcg gaatcgtttt ccgggacgcc   5040
ggctggatga tcctccagcg cggggatctc atgctggagt tcttcgccca ccccaacttg   5100
tttattgcag cttataatgg ttacaaataa agcaatagca tcacaaattt cacaaataaa   5160
gcattttttt cactgcattc tagttgtggt ttgtccaaac tcatcaatgt atcttatcat   5220
gtctgtatac cgtcgacctc tagctagagc ttggcgtaat catggtcata gctgtttcct   5280
gtgtgaaatt gttatccgct cacaattcca cacaacatac gagccggaag cataaagtgt   5340
aaagcctggg gtgcctaatg agtgagctaa ctcacattaa ttgcgttgcg ctcactgccc   5400
gctttccagt cgggaaacct gtcgtgccag ctgcattaat gaatcggcca acgcgcgggg   5460
agaggcggtt tgcgtattgg gcgctcttcc gcttcctcgc tcactgactc gctgcgctcg   5520
gtcgttcggc tgcggcgagc ggtatcagct cactcaaagg cggtaatacg gttatccaca   5580
gaatcagggg ataacgcagg aaagaacatg tgagcaaaag gccagcaaaa ggccaggaac   5640
cgtaaaaagg ccgcgttgct ggcgtttttc cataggctcc gcccccctga cgagcatcac   5700
aaaaatcgac gctcaagtca gaggtggcga aacccgacag gactataaag ataccaggcg   5760
tttccccctg gaagctccct cgtgcgctct cctgttccga ccctgccgct taccggatac   5820
ctgtccgcct ttctcccttc gggaagcgtg gcgctttctc aatgctcacg ctgtaggtat   5880
ctcagttcgg tgtaggtcgt tcgctccaag ctgggctgtg tgcacgaacc ccccgttcag   5940
cccgaccgct gcgccttatc cggtaactat cgtcttgagt ccaacccggt aagacacgac   6000
ttatcgccac tggcagcagc cactggtaac aggattagca gagcgaggta tgtaggcggt   6060
gctacagagt tcttgaagtg gtggcctaac tacggctaca ctagaaggac agtatttggt   6120
atctgcgctc tgctgaagcc agttaccttc ggaaaaagag ttggtagctc ttgatccggc   6180
aaacaaacca ccgctggtag cggtggtttt tttgtttgca agcagcagat tacgcgcaga   6240
aaaaaaggat ctcaagaaga tcctttgatc ttttctacgg ggtctgacgc tcagtggaac   6300
gaaaactcac gttaagggat tttggtcatg agattatcaa aaaggatctt cacctagatc   6360
cttttaaatt aaaaatgaag ttttaaatca atctaaagta tatatgagta aacttggtct   6420
gacagttacc aatgcttaat cagtgaggca cctatctcag cgatctgtct atttcgttca   6480
tccatagttg cctgactccc cgtcgtgtag ataactacga tacgggaggg cttaccatct   6540
ggccccagtg ctgcaatgat accgcgagac ccacgctcac cggctccaga tttatcagca   6600
ataaaccagc cagccggaag ggccgagcgc agaagtggtc ctgcaacttt atccgcctcc   6660
atccagtcta ttaattgttg ccgggaagct agagtaagta gttcgccagt taatagtttg   6720
```

-continued

```
cgcaacgttg ttgccattgc tacaggcatc gtggtgtcac gctcgtcgtt tggtatggct   6780

tcattcagct ccggttccca acgatcaagg cgagttacat gatcccccat gttgtgcaaa   6840

aaagcggtta gctccttcgg tcctccgatc gttgtcagaa gtaagttggc cgcagtgtta   6900

tcactcatgg ttatggcagc actgcataat tctcttactg tcatgccatc cgtaagatgc   6960

ttttctgtga ctggtgagta ctcaaccaag tcattctgag aatagtgtat gcggcgaccg   7020

agttgctctt gcccggcgtc aatacgggat aataccgcgc cacatagcag aactttaaaa   7080

gtgctcatca ttggaaaacg ttcttcgggg cgaaaactct caaggatctt accgctgttg   7140

agatccagtt cgatgtaacc cactcgtgca cccaactgat cttcagcatc ttttactttc   7200

accagcgttt ctgggtgagc aaaaacagga aggcaaaatg ccgcaaaaaa gggaataagg   7260

gcgacacgga aatgttgaat actcatactc ttcctttttc aatattattg aagcatttat   7320

cagggttatt gtctcatgag cggatacata tttgaatgta tttagaaaaa taaacaaata   7380

ggggttccgc gcacatttcc ccgaaaagtg ccacctgacg tc                      7422
```

<210> SEQ ID NO 2
<211> LENGTH: 10139
<212> TYPE: DNA
<213> ORGANISM: Artificial
<220> FEATURE:
<223> OTHER INFORMATION: Vector

<400> SEQUENCE: 2

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattgccc    960

ttattcctca gtgacccagg agctgacaca ctatggcgca cgtccgaggc ttgcagctgc   1020

ctggctgcct ggccctggct gccctgtgta gccttgtgca cagccagcat gtgttcctgg   1080

ctcctcagca agcacggtcg ctgctccagc gggtccggcg agccaacacc ttcttggagg   1140

aggtgcgcaa gggcaacctg gagcgagagt gcgtggagga gacgtgcagc tacgaggagg   1200

ccttcgaggc tctggagtcc tccacggcta cggatgtgtt ctgggccaag tacacagctt   1260

gtgagacagc gaggacgcct cgagataagc ttgctgcatg tctggaaggt aactgtgctg   1320
```

-continued

```
agggtctggg tacgaactac cgagggcatg tgaacatcac ccggtcaggc attgagtgcc   1380
agctatggag gagtcgctac ccacataagc ctgaaatcaa ctccactacc catcctgggg   1440
ccgacctaca ggagaatttc tgccgcaacc ccgacagcag caccacggga ccctggtgct   1500
acactacaga ccccaccgtg aggaggcagg aatgcagcat ccctgtctgt ggccaggatc   1560
aagtcactgt agcgatgact ccacgctccg aaggctccag tgtgaatctg tcacctccat   1620
tggagcagtg tgtccctgat cgggggcagc agtaccaggg gcgcctggcg gtgaccacac   1680
atgggctccc ctgcctggcc tgggccagcg cacaggccaa ggccctgagc aagcaccagg   1740
acttcaactc agctgtgcag ctggtggaga acttctgccg caacccagac ggggatgagg   1800
agggcgtgtg gtgctatgtg gccgggaagc ctggcgactt tgggtactgc gacctcaact   1860
attgtgagga ggccgtggag gaggagacag gagatgggct ggatgaggac tcagacaggg   1920
ccatcgaagg gcgtaccgcc accagtgagt accagacttt cttcaatccg aggacctttg   1980
gctcgggaga ggcagactgt gggctgcgac ctctgttcga gaagaagtcg ctggaggaca   2040
aaaccgaaag agagctcctg gaatcctaca tcgacgggcg cattgtggag ggctcggatg   2100
cagagatcgg catgtcacct tggcaggtga tgcttttccg gaagagtccc caggagctgc   2160
tgtgtggggc cagcctcatc agtgaccgct gggtcctcac cgccgcccac tgcctcctgt   2220
acccgccctg ggacaagaac ttcaccgaga atgaccttct ggtgcgcatt ggcaagcact   2280
cccgcaccag gtacgagcga aacattgaaa agatatccat gttggaaaag atctacatcc   2340
accccaggta caactggcgg gagaacctgg accgggacat tgccctgatg aagctgaaga   2400
agcctgttgc cttcagtgac tacattcacc ctgtgtgtct gcccgacagg gagacggcag   2460
ccagcttgct ccaggctgga tacaaggggc gggtgacagg ctggggcaac ctgaaggaga   2520
cgtggacagc caacgttggt aaggggcagc ccagtgtcct gcaggtggtg aacctgccca   2580
ttgtggagcg gccggtctgc aaggactcca cccggatccg catcactgac aacatgttct   2640
gtgctggtta caagcctgat gaagggaaac gaggggatgc ctgtgaaggt gacagtgggg   2700
gaccctttgt catgaagagc ccctttaaca accgctggta tcaaatgggc atcgtctcat   2760
ggggtgaagg ctgtgaccgg gatgggaaat atggcttcta cacacatgtg ttccgcctga   2820
agaagtggat acagaaggtc attgatcagt ttggagagta gaagggcaat tctgcagata   2880
tccagcacag tggcggccgc tcgagtctag agggcccgtt taaacccgct gatcagcctc   2940
gactgtgcct tctagttgcc agccatctgt tgtttgcccc tcccccgtgc cttccttgac   3000
cctggaaggt gccactccca ctgtcctttc ctaataaaat gaggaaattg catcgcattg   3060
tctgagtagg tgtcattcta ttctgggggg tggggtgggg caggacagca agggggagga   3120
ttgggaagac aatagcaggc atgctgggga tgcggtgggc tctatggctt ctgaggcgga   3180
aagaaccagc tggggctcta gggggtatcc ccacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcaccttc gaccccaaaa   3420
aacttgatta gggctgtgga atgtgtgtca gttagggtgt ggaaagtccc caggctcccc   3480
agcaggcaga agtatgcaaa gcatgcatct caattagtca gcaaccaggt gtggaaagtc   3540
cccaggctcc ccagcaggca gaagtatgca aagcatgcat ctcaattagt cagcaaccat   3600
agtcccgccc ctaactccgc ccatcccgcc cctaactccg cccagttccg cccattctcc   3660
gccccatggc tgactaattt tttttattta tgcagaggcc gaggccgcct cggcctctga   3720
```

-continued

```
gctattccag aagtagtgag gaggcttttt tggaggccta ggcttttgca aaaagctctc   3780
tggctaacta gagaacccac tgcttactgg cttatcgaaa ttaatacgac tcactatagg   3840
gagacccaag ctggctagcg tttaaactta agcttggtac cgagctcgga tccactagtc   3900
cagtgtggtg gaattgccct ttccgcagag caatggcggt gtctgccggg tccgcgcgga   3960
cctcgcccag ctcagataaa gtacagaaag acaaggctga actgatctca gggcccaggc   4020
aggacagccg aatagggaaa ctcttgggtt ttgagtggac agatttgtcc agttggcgga   4080
ggctggtgac cctgctgaat cgaccaacgg accctgcaag cttagctgtc tttcgttttc   4140
tttttgggtt cttgatggtg ctagacattc cccaggagcg ggggctcagc tctctggacc   4200
ggaaatacct tgatgggctg gatgtgtgcc gcttcccctt gctggatgcc ctacgcccac   4260
tgccacttga ctggatgtat cttgtctaca ccatcatgtt tctgggggca ctgggcatga   4320
tgctgggcct gtgctaccgg ataagctgtg tgttattcct gctgccatac tggtatgtgt   4380
ttctcctgga caagacatca tggaacaacc actcctatct gtatgggttg ttggcctttc   4440
agctaacatt catggatgca aaccactact ggtctgtgga cggtctgctg aatgcccata   4500
ggaggaatgc ccacgtgccc ctttggaact atgcagtgct ccgtggccag atcttcattg   4560
tgtacttcat tgcgggtgtg aaaaagctgg atgcagactg ggttgaaggc tattccatgg   4620
aatatttgtc ccggcactgg ctcttcagtc ccttcaaact gctgttgtct gaggagctga   4680
ctagcctgct ggtcgtgcac tggggtgggc tgctgcttga cctctcagct ggtttcctgc   4740
tctttttga tgtctcaaga tccattggcc tgttctttgt gtcctacttc cactgcatga   4800
attcccagct tttcagcatt ggtatgttct cctacgtcat gctggccagc agccctctct   4860
tctgctcccc tgagtggcct cggaagctgg tgtcctactg cccccgaagg ttgcaacaac   4920
tgttgcccct caaggcagcc cctcagccca gtgtttcctg tgtgtataag aggagccggg   4980
gcaaaagtgg ccagaagcca gggctgcgcc atcagctggg agctgccttc accctgctct   5040
acctcctgga gcagctattc ctgccctatt ctcattttct cacccagggc tataacaact   5100
ggacaaatgg gctgtatggc tattcctggg acatgatggt gcactcccgc tcccaccagc   5160
acgtgaagat cacctaccgt gatggccgca ctggcgaact gggctacctt aaccctgggg   5220
tatttacaca gagtcggcga tggaaggatc atgcagacat gctgaagcaa tatgccactt   5280
gcctgagccg cctgcttccc aagtataatg tcactgagcc ccagatctac tttgatattt   5340
gggtctccat caatgaccgc ttccagcaga ggatttttga ccctcgtgtg gacatcgtgc   5400
aggccgcttg gtcacccttt cagcgcacat cctgggtgca accactcttg atggacctgt   5460
ctccctggag ggccaagtta caggaaatca agagcagcct agacaaccac actgaggtgg   5520
tcttcattgc agatttccct ggactgcact tggagaattt tgtgagtgaa gacctgggca   5580
acactagcat ccagctgctg cagggggaag tgactgtgga gcttgtggca gaacagaaga   5640
accagactct tcgagaggga gaaaaaatgc agttgcctgc tggtgagtac cataaggtgt   5700
atacgacatc acctagccct tcttgctaca tgtacgtcta tgtcaacact acagagcttg   5760
cactggagca agacctggca tatctgcaag aattaaagga aaaggtggag aatggaagtg   5820
aaacagggcc tctacccccca gagctgcagc ctctgttgga aggggaagta aaagggggcc   5880
ctgagccaac acctctggtt cagacctttc ttagacgcca acaaaggctc caggagattg   5940
aacgccggcg aaatactcct ttccatgagc gattcttccg cttcttgttg cgaaagctct   6000
atgtctttcg ccgcagcttc ctgatgactt gtatctcact tcgaaatctg atattaggcc   6060
```

-continued

```
gtccttccct ggagcagctg gcccaggagg tgacttatgc aaacttgaga ccctttgagg   6120
cagttggaga actgaatccc tcaaacacgg attcttcaca ttctaatcct cctgagtcaa   6180
atcctgatcc tgtccactca gagttctgaa gggggccaga tgttggaagg gcaattcgag   6240
tctagagggc ccgccctgat agacggtttt tcgccctttg acgttggagt ccacgttctt   6300
taatagtgga ctcttgttcc aaactggaac aacactcaac cctatctcgg tctattcttt   6360
tgatttataa gggattttgc cgatttcggc ctattggtta aaaaatgagc tgatttaaca   6420
aaaatttaac gcgaattaat tctgtggaat gtgtgtcagt tagggtgtgg aaagtcccca   6480
ggctccccag caggcagaag tatgcaaagc atgcatctca attagtcagc aaccaggtgt   6540
ggaaagtccc caggctcccc agcaggcaga agtatgcaaa gcatgcatct caattagtca   6600
gcaaccatag tcccgcccct aactccgccc atcccgcccc taactccgcc cagttccgcc   6660
cattctccgc cccatggctg actaattttt tttatttatg cagaggccga ggccgcctct   6720
gcctctgagc tattccagaa gtagtgagga ggcttttttg gaggcctagg cttttgcaaa   6780
aagctcccgg gagcttgtat atccattttc ggatctgatc aagagacagg atgaggatcg   6840
tttcgcatga ttgaacaaga tggattgcac gcaggttctc cggccgcttg ggtggagagg   6900
ctattcggct atgactgggc acaacagaca atcggctgct ctgatgccgc cgtgttccgg   6960
ctgtcagcgc aggggcgccc ggttcttttt gtcaagaccg acctgtccgg tgccctgaat   7020
gaactgcagg acgaggcagc gcggctatcg tggctggcca cgacgggcgt tccttgcgca   7080
gctgtgctcg acgttgtcac tgaagcggga agggactggc tgctattggg cgaagtgccg   7140
gggcaggatc tcctgtcatc tcaccttgct cctgccgaga aagtatccat catggctgat   7200
gcaatgcggc ggctgcatac gcttgatccg gctacctgcc cattcgacca ccaagcgaaa   7260
catcgcatcg agcgagcacg tactcggatg gaagccggtc ttgtcgatca ggatgatctg   7320
gacgaagagc atcaggggct cgcgccagcc gaactgttcg ccaggctcaa ggcgcgcatg   7380
cccgacggcg aggatctcgt cgtgacccat ggcgatgcct gcttgccgaa tatcatggtg   7440
gaaaatggcc gcttttctgg attcatcgac tgtggccggc tgggtgtggc ggaccgctat   7500
caggacatag cgttggctac ccgtgatatt gctgaagagc ttggcggcga atgggctgac   7560
cgcttcctcg tgctttacgg tatcgccgct cccgattcgc agcgcatcgc cttctatcgc   7620
cttcttgacg agttcttctg agcgggactc tggggttcga aatgaccgac caagcgacgc   7680
ccaacctgcc atcacgagat ttcgattcca ccgccgcctt ctatgaaagg ttgggcttcg   7740
gaatcgtttt ccgggacgcc ggctggatga tcctccagcg cggggatctc atgctggagt   7800
tcttcgccca ccccaacttg tttattgcag cttataatgg ttacaaataa agcaatagca   7860
tcacaaattt cacaaataaa gcattttttt cactgcattc tagttgtggt ttgtccaaac   7920
tcatcaatgt atcttatcat gtctgtatac cgtcgacctc tagctagagc ttggcgtaat   7980
catggtcata gctgtttcct gtgtgaaatt gttatccgct cacaattcca cacaacatac   8040
gagccggaag cataaagtgt aaagcctggg gtgcctaatg agtgagctaa ctcacattaa   8100
ttgcgttgcg ctcactgccc gctttccagt cgggaaacct gtcgtgccag ctgcattaat   8160
gaatcggcca acgcgcgggg agaggcggtt tgcgtattgg gcgctcttcc gcttcctcgc   8220
tcactgactc gctgcgctcg gtcgttcggc tgcggcgagc ggtatcagct cactcaaagg   8280
cggtaatacg gttatccaca gaatcagggg ataacgcagg aaagaacatg tgagcaaaag   8340
gccagcaaaa ggccaggaac cgtaaaaagg ccgcgttgct ggcgtttttc cataggctcc   8400
gcccccctga cgagcatcac aaaaatcgac gctcaagtca gaggtggcga aacccgacag   8460
```

```
gactataaag ataccaggcg tttccccctg gaagctccct cgtgcgctct cctgttccga   8520

ccctgccgct taccggatac ctgtccgcct ttctcccttc gggaagcgtg gcgctttctc   8580

atagctcacg ctgtaggtat ctcagttcgg tgtaggtcgt tcgctccaag ctgggctgtg   8640

tgcacgaacc ccccgttcag cccgaccgct gcgccttatc cggtaactat cgtcttgagt   8700

ccaacccggt aagacacgac ttatcgccac tggcagcagc cactggtaac aggattagca   8760

gagcgaggta tgtaggcggt gctacagagt tcttgaagtg gtggcctaac tacggctaca   8820

ctagaagaac agtatttggt atctgcgctc tgctgaagcc agttaccttc ggaaaaagag   8880

ttggtagctc ttgatccggc aaacaaacca ccgctggtag cggttttttt gtttgcaagc   8940

agcagattac gcgcagaaaa aaaggatctc aagaagatcc tttgatcttt tctacggggt   9000

ctgacgctca gtggaacgaa aactcacgtt aagggatttt ggtcatgaga ttatcaaaaa   9060

ggatcttcac ctagatcctt ttaaattaaa aatgaagttt taaatcaatc taaagtatat   9120

atgagtaaac ttggtctgac agttaccaat gcttaatcag tgaggcacct atctcagcga   9180

tctgtctatt tcgttcatcc atagttgcct gactccccgt cgtgtagata actacgatac   9240

gggagggctt accatctggc cccagtgctg caatgatacc gcgagaccca cgctcaccgg   9300

ctccagattt atcagcaata aaccagccag ccggaagggc cgagcgcaga agtggtcctg   9360

caactttatc cgcctccatc cagtctatta attgttgccg ggaagctaga gtaagtagtt   9420

cgccagttaa tagtttgcgc aacgttgttg ccattgctac aggcatcgtg gtgtcacgct   9480

cgtcgtttgg tatggcttca ttcagctccg gttcccaacg atcaaggcga gttacatgat   9540

cccccatgtt gtgcaaaaaa gcggttagct ccttcggtcc tccgatcgtt gtcagaagta   9600

agttggccgc agtgttatca ctcatggtta tggcagcact gcataattct cttactgtca   9660

tgccatccgt aagatgcttt tctgtgactg gtgagtactc aaccaagtca ttctgagaat   9720

agtgtatgcg gcgaccgagt tgctcttgcc cggcgtcaat acgggataat accgcgccac   9780

atagcagaac tttaaaagtg ctcatcattg gaaaacgttc ttcggggcga aaactctcaa   9840

ggatcttacc gctgttgaga tccagttcga tgtaacccac tcgtgcaccc aactgatctt   9900

cagcatcttt tactttcacc agcgtttctg ggtgagcaaa aacaggaagg caaaatgccg   9960

caaaaaaggg aataagggcg acacggaaat gttgaatact catactcttc ctttttcaat  10020

attattgaag catttatcag ggttattgtc tcatgagcgg atacatattt gaatgtattt  10080

agaaaaataa acaaataggg gttccgcgca catttccccg aaaagtgcca cctgacgtc   10139
```

<210> SEQ ID NO 3
<211> LENGTH: 26
<212> TYPE: DNA
<213> ORGANISM: Homo sapiens

<400> SEQUENCE: 3

```
attcctcagt gacccaggag ctgaca                                           26
```

<210> SEQ ID NO 4
<211> LENGTH: 42
<212> TYPE: DNA
<213> ORGANISM: Homo sapiens

<400> SEQUENCE: 4

```
ctactctcca aactgatcaa tgaccttctg tatccacttc tt                         42
```

<210> SEQ ID NO 5

-continued

<211> LENGTH: 23
<212> TYPE: DNA
<213> ORGANISM: Homo sapiens

<400> SEQUENCE: 5
tccgcagagc aatggcggtg tct 23

<210> SEQ ID NO 6
<211> LENGTH: 24
<212> TYPE: DNA
<213> ORGANISM: Homo sapiens

<400> SEQUENCE: 6
ccaacatctg gccccttcag aact 24

<210> SEQ ID NO 7
<211> LENGTH: 24
<212> TYPE: DNA
<213> ORGANISM: Homo sapiens

<400> SEQUENCE: 7
acacctctgg ttcagacctt tctt 24

<210> SEQ ID NO 8
<211> LENGTH: 24
<212> TYPE: DNA
<213> ORGANISM: Homo sapiens

<400> SEQUENCE: 8
aatcgctcat ggaaaggagt attt 24

<210> SEQ ID NO 9
<211> LENGTH: 27
<212> TYPE: DNA
<213> ORGANISM: Homo sapiens

<400> SEQUENCE: 9
caacaaaggc tccaggagat tgaacgc 27

<210> SEQ ID NO 10
<211> LENGTH: 22
<212> TYPE: DNA
<213> ORGANISM: Homo sapiens

<400> SEQUENCE: 10
tggaggacaa aaccgaaaga ga 22

<210> SEQ ID NO 11
<211> LENGTH: 18
<212> TYPE: DNA
<213> ORGANISM: Homo sapiens

<400> SEQUENCE: 11
catccgagcc ctccacaa 18

<210> SEQ ID NO 12
<211> LENGTH: 25
<212> TYPE: DNA
<213> ORGANISM: Homo sapiens

<400> SEQUENCE: 12
ctcctggaat cctacatcga cgggc 25

<210> SEQ ID NO 13
<211> LENGTH: 10238
<212> TYPE: DNA
<213> ORGANISM: Artificial
<220> FEATURE:
<223> OTHER INFORMATION: Vector

<400> SEQUENCE: 13

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattgccc    960
ttattcctca gtgacccagg agctgacaca ctatggcgca cgtccgaggc ttgcagctgc   1020
ctggctgcct ggccctggct gccctgtgta gccttgtgca cagccagcat gtgttcctgg   1080
ctcctcagca agcacggtcg ctgctccagc gggtccggcg agccaacacc ttcttggagg   1140
aggtgcgcaa gggcaacctg gagcgagagt gcgtggagga gacgtgcagc tacgaggagg   1200
ccttcgaggc tctggagtcc tccacggcta cggatgtgtt ctgggccaag tacacagctt   1260
gtgagacagc gaggacgcct cgagataagc ttgctgcatg tctggaaggt aactgtgctg   1320
agggtctggg tacgaactac cgagggcatg tgaacatcac ccggtcaggc attgagtgcc   1380
agctatggag gagtcgctac ccacataagc ctgaaatcaa ctccactacc catcctgggg   1440
ccgacctaca ggagaatttc tgccgcaacc ccgacagcag caccacggga ccctggtgct   1500
acactacaga ccccaccgtg aggaggcagg aatgcagcat ccctgtctgt ggccaggatc   1560
aagtcactgt agcgatgact ccacgctccg aaggctccag tgtgaatctg tcacctccat   1620
tggagcagtg tgtccctgat cgggggcagc agtaccaggg gcgcctggcg gtgaccacac   1680
atgggctccc ctgcctggcc tgggccagcg cacaggccaa ggccctgagc aagcaccagg   1740
acttcaactc agctgtgcag ctggtggaga acttctgccg caacccagac ggggatgagg   1800
agggcgtgtg gtgctatgtg gccgggaagc ctggcgactt tgggtactgc gacctcaact   1860
attgtgagga ggccgtggag gaggagacag gagatgggct ggatgaggac tcagacaggg   1920
ccatcgaagg gcgtaccgcc accagtgagt accagacttt cttcaatccg aggacctttg   1980
gctcgggaga ggcagactgt gggctgcgac ctctgttcga gaagaagtcg ctggaggaca   2040
aaaccgaaag agagctcctg gaatcctaca tcgacgggcg cattgtggag ggctcggatg   2100
```

-continued

```
cagagatcgg catgtcacct tggcaggtga tgcttttccg gaagagtccc caggagctgc   2160
tgtgtggggc cagcctcatc agtgaccgct gggtcctcac cgccgcccac tgcctcctgt   2220
acccgccctg ggacaagaac ttcaccgaga atgaccttct ggtgcgcatt ggcaagcact   2280
cccgcaccag gtacgagcga aacattgaaa agatatccat gttggaaaag atctacatcc   2340
accccaggta caactggcgg gagaacctgg accgggacat tgccctgatg aagctgaaga   2400
agcctgttgc cttcagtgac tacattcacc ctgtgtgtct gcccgacagg gagacggcag   2460
ccagcttgct ccaggctgga tacaaggggc gggtgacagg ctggggcaac ctgaaggaga   2520
cgtggacagc caacgttggt aaggggcagc ccagtgtcct gcaggtggtg aacctgccca   2580
ttgtggagcg gccggtctgc aaggactcca cccggatccg catcactgac aacatgttct   2640
gtgctggtta caagcctgat gaagggaaac gaggggatgc ctgtgaaggt gacagtgggg   2700
gaccctttgt catgaagagc ccctttaaca accgctggta tcaaatgggc atcgtctcat   2760
ggggtgaagg ctgtgaccgg gatgggaaat atggcttcta cacacatgtg ttccgcctga   2820
agaagtggat acagaaggtc attgatcagt ttggagagta gaagggcaat tctgcagata   2880
tccagcacag tggcggccgc tcggttccta gagggcccgt ttaaacccgc tgatcagcct   2940
cgactgtgcc ttctagttgc cagccatctg ttgtttgccc ctcccccgtg ccttccttga   3000
ccctggaagg tgccactccc actgtccttt cctaataaaa tgaggaaatt gcatcgcatt   3060
gtctgagtag gtgtcattct attctggggg gtggggtggg gcaggacagc aagggggagg   3120
attgggaaga caatagcagg catgctgggg atgcggtggg ctctatggct tctgaggcgg   3180
aaagaaccag ctggggctct agggggtatc cccacgcgcc ctgtagcggc gcattaagcg   3240
cggcgggtgt ggtggttacg cgcagcgtga ccgctacact tgccagcgcc ctagcgcccg   3300
ctcctttcgc tttcttccct tcctttctcg ccacgttcgc cggctttccc cgtcaagctc   3360
taaatcgggg gctcccttta gggttccgat ttagtgcttt acggcacctc gaccccaaaa   3420
aacttgatta gggtgatggt tcacatcgat gcaatttcct cattttatta ggaaaggaca   3480
gtgggagtgg caccttccag ggtcaaggaa ggcacggggg aggggcaaac aacagatggc   3540
tggcaactag aaggcacagt cgaggctgat cagcgggttt aaacgggccc tctagactcg   3600
aattgccctt ccaacatctg gcccccttca gaactctgag tggacaggat caggatttga   3660
ctcaggagga ttagaatgtg aagaatccgt gtttgaggga ttcagttctc caactgcctc   3720
aaagggtctc aagtttgcat aagtcacctc ctgggccagc tgctccaggg aaggacggcc   3780
taatatcaga tttcgaagtg agatacaagt catcaggaag ctgcggcgaa agacatagag   3840
ctttcgcaac aagaagcgga agaatcgctc atggaaagga gtatttcgcc ggcgttcaat   3900
ctcctggagc ctttgttggc gtctaagaaa ggtctgaacc agaggtgttg gctcagggcc   3960
ccctttttact tcccccttcca acagaggctg cagctctggg ggtagaggcc ctgtttcact   4020
tccattctcc acctttttcct ttaattcttg cagatatgcc aggtcttgct ccagtgcaag   4080
ctctgtagtg ttgacataga cgtacatgta gcaagaaggg ctaggtgatg tcgtatacac   4140
cttatggtac tcaccagcag gcaactgcat tttttctccc tctcgaagag tctggttctt   4200
ctgttctgcc acaagctcca cagtcacttc cccctgcagc agctggatgc tagtgttgcc   4260
caggtcttca ctcacaaaat tctccaagtg cagtccaggg aaatctgcaa tgaagaccac   4320
ctcagtgtgg ttgtctaggc tgctcttgat ttcctgtaac ttggccctcc agggagacag   4380
gtccatcaag agtggttgca cccaggatgt gcgctgaaag ggtgaccaag cggcctgcac   4440
gatgtccaca cgagggtcaa aaatcctctg ctggaagcgg tcattgatgg agacccaaat   4500
```

-continued

```
atcaaagtag atctggggct cagtgacatt atacttggga agcaggcggc tcaggcaagt   4560
ggcatattgc ttcagcatgt ctgcatgatc cttccatcgc cgactctgtg taaatacccc   4620
agggttaagg tagcccagtt cgccagtgcg gccatcacgg taggtgatct tcacgtgctg   4680
gtgggagcgg gagtgcacca tcatgtccca ggaatagcca tacagcccat ttgtccagtt   4740
gttatagccc tgggtgagaa aatgagaata gggcaggaat agctgctcca ggaggtagag   4800
cagggtgaag gcagctccca gctgatggcg cagccctggc ttctggccac ttttgccccg   4860
gctcctctta tacacacagg aaacactggg ctgaggggct gccttgaggg gcaacagttg   4920
ttgcaacctt cgggggcagt aggacaccag cttccgaggc cactcagggg agcagaagag   4980
agggctgctg gccagcatga cgtaggagaa cataccaatg ctgaaaagct gggaattcat   5040
gcagtggaag taggacacaa agaacaggcc aatggatctt gagacatcaa aaaagagcag   5100
gaaaccagct gagaggtcaa gcagcagccc accccagtgc acgaccagca ggctagtcag   5160
ctcctcagac aacagcagtt tgaagggact gaagagccag tgccgggaca aatattccat   5220
ggaatagcct tcaacccagt ctgcatccag ctttttcaca cccgcaatga agtacacaat   5280
gaagatctgg ccacggagca ctgcatagtt ccaaaggggc acgtgggcat tcctcctatg   5340
ggcattcagc agaccgtcca cagaccagta gtggtttgca tccatgaatg ttagctgaaa   5400
ggccaacaac ccatacagat aggagtggtt gttccatgat gtcttgtcca ggagaaacac   5460
ataccagtat ggcagcagga ataacacaca gcttatccgg tagcacaggc ccagcatcat   5520
gcccagtgcc cccagaaaca tgatggtgta gacaagatac atccagtcaa gtggcagtgg   5580
gcgtagggca tccagcaagg ggaagcggca cacatccagc ccatcaaggt atttccggtc   5640
cagagagctg agcccccgct cctggggaat gtctagcacc atcaagaacc caaaaagaaa   5700
acgaaagaca gctaagcttg cagggtccgt tggtcgattc agcagggtca ccagcctccg   5760
ccaactggac aaatctgtcc actcaaaacc caagagtttc cctattcggc tgtcctgcct   5820
gggccctgag atcagttcag ccttgtcttt ctgtacttta tctgagctgg gcgaggtccg   5880
cgcggacccg gcagacaccg ccattgctct gcggaaaggg caattccacc acactggact   5940
agtggatccg agctcggtac caagcttaag tttaaacgct agccagcttg ggtctcccta   6000
tagtgagtcg tattaatttc gataagccag taagcagtgg gttctctagt tagccagaga   6060
gctttttgca aaagcctagg cctccaaaaa agcctcctca ctacttctgg aatagctcag   6120
aggccgaggc ggcctcggcc tctgcataaa taaaaaaaat tagtcagcca tggggcggag   6180
aatgggcgga actgggcgga gttaggggcg ggatgggcgg agttaggggc gggactatgg   6240
ttgctgacta attgagatgc atgctttgca tacttctgcc tgctggggag cctggggact   6300
ttccacaccc taactgacac acattccaca gccggatcga tgtgggccat cgccctgata   6360
gacggttttt cgccctttga cgttggagtc cacgttcttt aatagtggac tcttgttcca   6420
aactggaaca acactcaacc ctatctcggt ctattctttt gatttataag ggattttgcc   6480
gatttcggcc tattggttaa aaaatgagct gatttaacaa aaatttaacg cgaattaatt   6540
ctgtggaatg tgtgtcagtt agggtgtgga aagtccccag gctccccagc aggcagaagt   6600
atgcaaagca tgcatctcaa ttagtcagca accaggtgtg gaaagtcccc aggctcccca   6660
gcaggcagaa gtatgcaaag catgcatctc aattagtcag caaccatagt cccgccccta   6720
actccgccca tcccgcccct aactccgccc agttccgccc attctccgcc ccatggctga   6780
ctaatttttt ttatttatgc agaggccgag gccgcctctg cctctgagct attccagaag   6840
```

-continued

```
tagtgaggag gctttttgg aggcctaggc ttttgcaaaa agctcccggg agcttgtata   6900
tccattttcg gatctgatca agagacagga tgaggatcgt ttcgcatgat tgaacaagat   6960
ggattgcacg caggttctcc ggccgcttgg gtggagaggc tattcggcta tgactgggca   7020
caacagacaa tcggctgctc tgatgccgcc gtgttccggc tgtcagcgca ggggcgcccg   7080
gttctttttg tcaagaccga cctgtccggt gccctgaatg aactgcagga cgaggcagcg   7140
cggctatcgt ggctggccac gacgggcgtt ccttgcgcag ctgtgctcga cgttgtcact   7200
gaagcgggaa gggactggct gctattgggc gaagtgccgg ggcaggatct cctgtcatct   7260
caccttgctc ctgccgagaa agtatccatc atggctgatg caatgcggcg gctgcatacg   7320
cttgatccgg ctacctgccc attcgaccac caagcgaaac atcgcatcga gcgagcacgt   7380
actcggatgg aagccggtct tgtcgatcag gatgatctgg acgaagagca tcaggggctc   7440
gcgccagccg aactgttcgc caggctcaag gcgcgcatgc ccgacggcga ggatctcgtc   7500
gtgacccatg gcgatgcctg cttgccgaat atcatggtgg aaaatggccg cttttctgga   7560
ttcatcgact gtggccggct gggtgtggcg gaccgctatc aggacatagc gttggctacc   7620
cgtgatattg ctgaagagct tggcggcgaa tgggctgacc gcttcctcgt gctttacggt   7680
atcgccgctc ccgattcgca gcgcatcgcc ttctatcgcc ttcttgacga gttcttctga   7740
gcgggactct ggggttcgaa atgaccgacc aagcgacgcc caacctgcca tcacgagatt   7800
tcgattccac cgccgccttc tatgaaaggt tgggcttcgg aatcgttttc cgggacgccg   7860
gctggatgat cctccagcgc ggggatctca tgctggagtt cttcgcccac cccaacttgt   7920
ttattgcagc ttataatggt tacaaataaa gcaatagcat cacaaatttc acaaataaag   7980
catttttttc actgcattct agttgtggtt tgtccaaact catcaatgta tcttatcatg   8040
tctgtatacc gtcgacctct agctagagct tggcgtaatc atggtcatag ctgtttcctg   8100
tgtgaaattg ttatccgctc acaattccac acaacatacg agccggaagc ataaagtgta   8160
aagcctgggg tgcctaatga gtgagctaac tcacattaat tgcgttgcgc tcactgcccg   8220
ctttccagtc gggaaacctg tcgtgccagc tgcattaatg aatcggccaa cgcgcgggga   8280
gaggcggttt gcgtattggg cgctcttccg cttcctcgct cactgactcg ctgcgctcgg   8340
tcgttcggct gcggcgagcg gtatcagctc actcaaaggc ggtaatacgg ttatccacag   8400
aatcagggga taacgcagga aagaacatgt gagcaaaagg ccagcaaaag gccaggaacc   8460
gtaaaaaggc cgcgttgctg gcgtttttcc ataggctccg cccccctgac gagcatcaca   8520
aaaatcgacg ctcaagtcag aggtggcgaa acccgacagg actataaaga taccaggcgt   8580
ttccccctgg aagctccctc gtgcgctctc ctgttccgac cctgccgctt accggatacc   8640
tgtccgcctt tctcccttcg ggaagcgtgg cgctttctca tagctcacgc tgtaggtatc   8700
tcagttcggt gtaggtcgtt cgctccaagc tgggctgtgt gcacgaaccc cccgttcagc   8760
ccgaccgctg cgccttatcc ggtaactatc gtcttgagtc caacccggta agacacgact   8820
tatcgccact ggcagcagcc actggtaaca ggattagcag agcgaggtat gtaggcggtg   8880
ctacagagtt cttgaagtgg tggcctaact acggctacac tagaagaaca gtatttggta   8940
tctgcgctct gctgaagcca gttaccttcg gaaaaagagt tggtagctct tgatccggca   9000
aacaaaccac cgctggtagc ggtttttttg tttgcaagca gcagattacg cgcagaaaaa   9060
aaggatctca agaagatcct ttgatctttt ctacggggtc tgacgctcag tggaacgaaa   9120
actcacgtta agggattttg gtcatgagat tatcaaaaag gatcttcacc tagatccttt   9180
taaattaaaa atgaagtttt aaatcaatct aaagtatata tgagtaaact tggtctgaca   9240
```

-continued

```
gttaccaatg cttaatcagt gaggcaccta tctcagcgat ctgtctattt cgttcatcca   9300

tagttgcctg actccccgtc gtgtagataa ctacgatacg ggagggctta ccatctggcc   9360

ccagtgctgc aatgataccg cgagacccac gctcaccggc tccagattta tcagcaataa   9420

accagccagc cggaagggcc gagcgcagaa gtggtcctgc aactttatcc gcctccatcc   9480

agtctattaa ttgttgccgg gaagctagag taagtagttc gccagttaat agtttgcgca   9540

acgttgttgc cattgctaca ggcatcgtgg tgtcacgctc gtcgtttggt atggcttcat   9600

tcagctccgg ttcccaacga tcaaggcgag ttacatgatc ccccatgttg tgcaaaaaag   9660

cggttagctc cttcggtcct ccgatcgttg tcagaagtaa gttggccgca gtgttatcac   9720

tcatggttat ggcagcactg cataattctc ttactgtcat gccatccgta agatgctttt   9780

ctgtgactgg tgagtactca accaagtcat tctgagaata gtgtatgcgg cgaccgagtt   9840

gctcttgccc ggcgtcaata cgggataata ccgcgccaca tagcagaact ttaaaagtgc   9900

tcatcattgg aaaacgttct tcggggcgaa aactctcaag gatcttaccg ctgttgagat   9960

ccagttcgat gtaacccact cgtgcaccca actgatcttc agcatctttt actttcacca  10020

gcgtttctgg gtgagcaaaa acaggaaggc aaaatgccgc aaaaaaggga ataagggcga  10080

cacggaaatg ttgaatactc atactcttcc tttttcaata ttattgaagc atttatcagg  10140

gttattgtct catgagcgga tacatatttg aatgtattta gaaaaataaa caaatagggg  10200

ttccgcgcac atttccccga aaagtgccac ctgacgtc                         10238
```

<210> SEQ ID NO 14
<211> LENGTH: 9683
<212> TYPE: DNA
<213> ORGANISM: Artificial
<220> FEATURE:
<223> OTHER INFORMATION: Vector

<400> SEQUENCE: 14

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattgccc    960

ttattcctca gtgacccagg agctgacaca cttagaaggg caattctgca gatcaccatg   1020
```

-continued

```
cagcgcgtga acatgatcat ggcagaatca ccaggcctca tcaccatctg ccttttagga   1080
tatctactca gtgctgaatg tacagttttt cttgatcatg aaaacgccaa caaaattctg   1140
aatcggccaa agaggtataa ttcaggtaaa ttggaagagt ttgttcaagg gaaccttgag   1200
agagaatgta tggaagaaaa gtgtagtttt gaagaagcac gagaagtttt tgaaaacact   1260
gaaagaacaa ctgaattttg gaagcagtat gttgatggag atcagtgtga gtccaatcca   1320
tgtttaaatg gcggcagttg caaggatgac attaattcct atgaatgttg gtgtcccttt   1380
ggatttgaag gaaagaactg tgaattagat gtaacatgta acattaagaa tggcagatgc   1440
gagcagtttt gtaaaaatag tgctgataac aaggtggttt gctcctgtac tgagggatat   1500
cgacttgcag aaaaccagaa gtcctgtgaa ccagcagtgc catttccatg tggaagagtt   1560
tctgtttcac aaacttctaa gctcacccgt gctgagactg tttttcctga tgtggactat   1620
gtaaattcta ctgaagctga aaccattttg gataacatca ctcaaagcac ccaatcattt   1680
aatgacttca ctcgggttgt tggtggagaa gatgccaaac caggtcaatt cccttggcag   1740
gttgttttga atggtaaagt tgatgcattc tgtggaggct ctatcgttaa tgaaaaatgg   1800
attgtaactg ctgcccactg tgttgaaact ggtgttaaaa ttacagttgt cgcaggtgaa   1860
cataatattg aggagacaga acatacagag caaaagcgaa atgtgattcg aattattcct   1920
caccacaact acaatgcagc tattaataag tacaaccatg acattgccct tctggaactg   1980
gacgaaccct tagtgctaaa cagctacgtt acacctattt gcattgctga caaggaatac   2040
acgaacatct tcctcaaatt tggatctggc tatgtaagtg gctggggaag ggtcttccac   2100
aaagggagat cagctttagt tcttcagtac cttagagttc cacttgttga ccgagccaca   2160
tgtcttcgat ctacaaagtt caccatctat aacaacatgt tctgtgctgg cttccatgaa   2220
ggaggtagag attcatgtca aggagatagt gggggacccc atgttactga agtggaaggg   2280
accagtttct taactggaat tattagctgg ggtgaagagt gtgcaatgaa aggcaaatat   2340
ggaatatata ccaaggtatc ccggtatgtc aactggatta aggaaaaaac aaagctcact   2400
taatgaaaga tggatttcca aggatccagc acagtggcgg ccgctcgagt ctagagggcc   2460
cgtttaaacc cgctgatcag cctcgactgt gccttctagt tgccagccat ctgttgtttg   2520
cccctccccc gtgccttcct tgaccctgga aggtgccact cccactgtcc tttcctaata   2580
aaatgaggaa attgcatcgc attgtctgag taggtgtcat tctattctgg ggggtggggt   2640
ggggcaggac agcaaggggg aggattggga agacaatagc aggcatgctg gggatgcggt   2700
gggctctatg gcttctgagg cggaaagaac cagctggggc tctagggggt atccccacgc   2760
gccctgtagc ggcgcattaa gcgcggcggg tgtggtggtt acgcgcagcg tgaccgctac   2820
acttgccagc gccctagcgc ccgctccttt cgctttcttc ccttcctttc tcgccacgtt   2880
cgccggcttt ccccgtcaag ctctaaatcg ggggctccct ttagggttcc gatttagtgc   2940
tttacggcac cttcgacccc aaaaaacttg attagggctg tggaatgtgt gtcagttagg   3000
gtgtggaaag tccccaggct ccccagcagg cagaagtatg caaagcatgc atctcaatta   3060
gtcagcaacc aggtgtggaa agtccccagg ctccccagca ggcagaagta tgcaaagcat   3120
gcatctcaat tagtcagcaa ccatagtccc gcccctaact ccgcccatcc cgcccctaac   3180
tccgcccagt tccgcccatt ctccgcccca tggctgacta atttttttta tttatgcaga   3240
ggccgaggcc gcctcggcct ctgagctatt ccagaagtag tgaggaggct tttttggagg   3300
cctaggcttt tgcaaaaagc tctctggcta actagagaac ccactgctta ctggcttatc   3360
gaaattaata cgactcacta tagggagacc caagctggct agcgtttaaa cttaagcttg   3420
```

-continued

```
gtaccgagct cggatccact agtccagtgt ggtggaattg ccctttccgc agagcaatgg   3480
cggtgtctgc cgggtccgcg cggacctcgc ccagctcaga taaagtacag aaagacaagg   3540
ctgaactgat ctcagggccc aggcaggaca gccgaatagg gaaactcttg ggttttgagt   3600
ggacagattt gtccagttgg cggaggctgg tgaccctgct gaatcgacca acggaccctg   3660
caagcttagc tgtctttcgt tttctttttg ggttcttgat ggtgctagac attccccagg   3720
agcgggggct cagctctctg gaccggaaat accttgatgg gctggatgtg tgccgcttcc   3780
ccttgctgga tgccctacgc ccactgccac ttgactggat gtatcttgtc tacaccatca   3840
tgtttctggg ggcactgggc atgatgctgg gcctgtgcta ccggataagc tgtgtgttat   3900
tcctgctgcc atactggtat gtgtttctcc tggacaagac atcatggaac aaccactcct   3960
atctgtatgg gttgttggcc tttcagctaa cattcatgga tgcaaaccac tactggtctg   4020
tggacggtct gctgaatgcc cataggagga atgcccacgt gccccttgg aactatgcag   4080
tgctccgtgg ccagatcttc attgtgtact tcattgcggg tgtgaaaaag ctggatgcag   4140
actgggttga aggctattcc atggaatatt tgtcccggca ctggctcttc agtcccttca   4200
aactgctgtt gtctgaggag ctgactagcc tgctggtcgt gcactggggt gggctgctgc   4260
ttgacctctc agctggtttc ctgctctttt ttgatgtctc aagatccatt ggcctgttct   4320
ttgtgtccta cttccactgc atgaattccc agcttttcag cattggtatg ttctcctacg   4380
tcatgctggc cagcagccct ctcttctgct cccctgagtg gcctcggaag ctggtgtcct   4440
actgcccccg aaggttgcaa caactgttgc cctcaaggc agcccctcag cccagtgttt   4500
cctgtgtgta taagaggagc cggggcaaaa gtggccagaa gccagggctg cgccatcagc   4560
tgggagctgc cttcaccctg ctctacctcc tggagcagct attcctgccc tattctcatt   4620
ttctcaccca gggctataac aactggacaa atgggctgta tggctattcc tgggacatga   4680
tggtgcactc ccgctcccac cagcacgtga agatcaccta ccgtgatggc cgcactggcg   4740
aactgggcta ccttaaccct ggggtattta cacagagtcg gcgatggaag gatcatgcag   4800
acatgctgaa gcaatatgcc acttgcctga gccgcctgct tcccaagtat aatgtcactg   4860
agccccagat ctactttgat atttgggtct ccatcaatga ccgcttccag cagaggattt   4920
ttgaccctcg tgtggacatc gtgcaggccg cttggtcacc ctttcagcgc acatcctggg   4980
tgcaaccact cttgatggac ctgtctccct ggagggccaa gttacaggaa atcaagagca   5040
gcctagacaa ccacactgag gtggtcttca ttgcagattt ccctggactg cacttggaga   5100
attttgtgag tgaagacctg ggcaacacta gcatccagct gctgcagggg gaagtgactg   5160
tggagcttgt ggcagaacag aagaaccaga ctcttcgaga gggagaaaaa atgcagttgc   5220
ctgctggtga gtaccataag gtgtatacga catcacctag cccttcttgc tacatgtacg   5280
tctatgtcaa cactacagag cttgcactgg agcaagacct ggcatatctg caagaattaa   5340
aggaaaaggt ggagaatgga agtgaaacag ggcctctacc cccagagctg cagcctctgt   5400
tggaaggga agtaaaaggg ggccctgagc caacacctct ggttcagacc tttcttagac   5460
gccaacaaag gctccaggag attgaacgcc ggcgaaatac tcctttccat gagcgattct   5520
tccgcttctt gttgcgaaag ctctatgtct ttcgccgcag cttcctgatg acttgtatct   5580
cacttcgaaa tctgatatta ggccgtcctt ccctggagca gctggcccag gaggtgactt   5640
atgcaaactt gagacccttt gaggcagttg gagaactgaa tccctcaaac acggattctt   5700
cacattctaa tcctcctgag tcaaatcctg atcctgtcca ctcagagttc tgaagggggc   5760
```

-continued

```
cagatgttgg aagggcaatt cgagtctaga gggcccgccc tgatagacgg tttttcgccc   5820
tttgacgttg gagtccacgt tctttaatag tggactcttg ttccaaactg gaacaacact   5880
caaccctatc tcggtctatt cttttgattt ataagggatt ttgccgattt cggcctattg   5940
gttaaaaaat gagctgattt aacaaaaatt taacgcgaat taattctgtg gaatgtgtgt   6000
cagttagggt gtggaaagtc cccaggctcc ccagcaggca gaagtatgca aagcatgcat   6060
ctcaattagt cagcaaccag gtgtggaaag tccccaggct ccccagcagg cagaagtatg   6120
caaagcatgc atctcaatta gtcagcaacc atagtcccgc ccctaactcc gcccatcccg   6180
cccctaactc cgcccagttc cgcccattct ccgccccatg gctgactaat tttttttatt   6240
tatgcagagg ccgaggccgc ctctgcctct gagctattcc agaagtagtg aggaggcttt   6300
tttggaggcc taggcttttg caaaaagctc ccgggagctt gtatatccat tttcggatct   6360
gatcaagaga caggatgagg atcgtttcgc atgattgaac aagatggatt gcacgcaggt   6420
tctccggccg cttgggtgga gaggctattc ggctatgact gggcacaaca gacaatcggc   6480
tgctctgatg ccgccgtgtt ccggctgtca gcgcaggggc gcccggttct ttttgtcaag   6540
accgacctgt ccggtgccct gaatgaactg caggacgagg cagcgcggct atcgtggctg   6600
gccacgacgg gcgttccttg cgcagctgtg ctcgacgttg tcactgaagc gggaagggac   6660
tggctgctat tgggcgaagt gccggggcag gatctcctgt catctcacct tgctcctgcc   6720
gagaaagtat ccatcatggc tgatgcaatg cggcggctgc atacgcttga tccggctacc   6780
tgcccattcg accaccaagc gaaacatcgc atcgagcgag cacgtactcg gatggaagcc   6840
ggtcttgtcg atcaggatga tctggacgaa gagcatcagg ggctcgcgcc agccgaactg   6900
ttcgccaggc tcaaggcgcg catgcccgac ggcgaggatc tcgtcgtgac ccatggcgat   6960
gcctgcttgc cgaatatcat ggtggaaaat ggccgctttt ctggattcat cgactgtggc   7020
cggctgggtg tggcggaccg ctatcaggac atagcgttgg ctacccgtga tattgctgaa   7080
gagcttggcg gcgaatgggc tgaccgcttc ctcgtgcttt acggtatcgc cgctcccgat   7140
tcgcagcgca tcgccttcta tcgccttctt gacgagttct tctgagcggg actctggggt   7200
tcgaaatgac cgaccaagcg acgcccaacc tgccatcacg agatttcgat tccaccgccg   7260
ccttctatga aaggttgggc ttcggaatcg ttttccggga cgccggctgg atgatcctcc   7320
agcgcgggga tctcatgctg gagttcttcg cccaccccaa cttgtttatt gcagcttata   7380
atggttacaa ataaagcaat agcatcacaa atttcacaaa taaagcattt ttttcactgc   7440
attctagttg tggtttgtcc aaactcatca atgtatctta tcatgtctgt ataccgtcga   7500
cctctagcta gagcttggcg taatcatggt catagctgtt tcctgtgtga aattgttatc   7560
cgctcacaat tccacacaac atacgagccg gaagcataaa gtgtaaagcc tggggtgcct   7620
aatgagtgag ctaactcaca ttaattgcgt tgcgctcact gcccgctttc cagtcgggaa   7680
acctgtcgtg ccagctgcat taatgaatcg gccaacgcgc ggggagaggc ggtttgcgta   7740
ttgggcgctc ttccgcttcc tcgctcactg actcgctgcg ctcggtcgtt cggctgcggc   7800
gagcggtatc agctcactca aaggcggtaa tacggttatc cacagaatca ggggataacg   7860
caggaaagaa catgtgagca aaaggccagc aaaaggccag gaaccgtaaa aaggccgcgt   7920
tgctggcgtt tttccatagg ctccgccccc ctgacgagca tcacaaaaat cgacgctcaa   7980
gtcagaggtg gcgaaacccg acaggactat aaagatacca ggcgtttccc cctggaagct   8040
ccctcgtgcg ctctcctgtt ccgaccctgc cgcttaccgg atacctgtcc gcctttctcc   8100
cttcgggaag cgtggcgctt tctcatagct cacgctgtag gtatctcagt tcggtgtagg   8160
```

-continued

```
tcgttcgctc caagctgggc tgtgtgcacg aaccccccgt tcagcccgac cgctgcgcct   8220
tatccggtaa ctatcgtctt gagtccaacc cggtaagaca cgacttatcg ccactggcag   8280
cagccactgg taacaggatt agcagagcga ggtatgtagg cggtgctaca gagttcttga   8340
agtggtggcc taactacggc tacactagaa gaacagtatt tggtatctgc gctctgctga   8400
agccagttac cttcggaaaa agagttggta gctcttgatc cggcaaacaa accaccgctg   8460
gtagcggttt ttttgtttgc aagcagcaga ttacgcgcag aaaaaaagga tctcaagaag   8520
atcctttgat cttttctacg gggtctgacg ctcagtggaa cgaaaactca cgttaaggga   8580
ttttggtcat gagattatca aaaaggatct tcacctagat ccttttaaat taaaaatgaa   8640
gttttaaatc aatctaaagt atatatgagt aaacttggtc tgacagttac caatgcttaa   8700
tcagtgaggc acctatctca gcgatctgtc tatttcgttc atccatagtt gcctgactcc   8760
ccgtcgtgta gataactacg atacgggagg gcttaccatc tggccccagt gctgcaatga   8820
taccgcgaga cccacgctca ccggctccag atttatcagc aataaaccag ccagccggaa   8880
gggccgagcg cagaagtggt cctgcaactt tatccgcctc catccagtct attaattgtt   8940
gccgggaagc tagagtaagt agttcgccag ttaatagttt gcgcaacgtt gttgccattg   9000
ctacaggcat cgtggtgtca cgctcgtcgt ttggtatggc ttcattcagc tccggttccc   9060
aacgatcaag gcgagttaca tgatccccca tgttgtgcaa aaaagcggtt agctccttcg   9120
gtcctccgat cgttgtcaga agtaagttgg ccgcagtgtt atcactcatg gttatggcag   9180
cactgcataa ttctcttact gtcatgccat ccgtaagatg cttttctgtg actggtgagt   9240
actcaaccaa gtcattctga gaatagtgta tgcggcgacc gagttgctct tgcccggcgt   9300
caatacggga taataccgcg ccacatagca gaactttaaa agtgctcatc attggaaaac   9360
gttcttcggg gcgaaaactc tcaaggatct taccgctgtt gagatccagt tcgatgtaac   9420
ccactcgtgc acccaactga tcttcagcat cttttacttt caccagcgtt tctgggtgag   9480
caaaaacagg aaggcaaaat gccgcaaaaa agggaataag ggcgacacgg aaatgttgaa   9540
tactcatact cttccttttt caatattatt gaagcattta tcagggttat tgtctcatga   9600
gcggatacat atttgaatgt atttagaaaa ataaacaaat aggggttccg cgcacatttc   9660
cccgaaaagt gccacctgac gtc                                          9683
```

<210> SEQ ID NO 15
<211> LENGTH: 9781
<212> TYPE: DNA
<213> ORGANISM: Artificial
<220> FEATURE:
<223> OTHER INFORMATION: Vector

<400> SEQUENCE: 15

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
```

-continued

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattgccc    960
ttattcctca gtgacccagg agctgacaca cttagaaggg caattctgca gataccatgc   1020
agcgcgtgaa catgatcatg gcagaatcac caggcctcat caccatctgc cttttaggat   1080
atctactcag tgctgaatgt acagtttttc ttgatcatga aaacgccaac aaaattctga   1140
atcggccaaa gaggtataat tcaggtaaat tggaagagtt tgttcaaggg aaccttgaga   1200
gagaatgtat ggaagaaaag tgtagttttg aagaagcacg agaagttttt gaaaacactg   1260
aaagaacaac tgaattttgg aagcagtatg ttgatggaga tcagtgtgag tccaatccat   1320
gtttaaatgg cggcagttgc aaggatgaca ttaattccta tgaatgttgg tgtccctttg   1380
gatttgaagg aaagaactgt gaattagatg taacatgtaa cattaagaat ggcagatgcg   1440
agcagttttg taaaaatagt gctgataaca aggtggtttg ctcctgtact gagggatatc   1500
gacttgcaga aaaccagaag tcctgtgaac cagcagtgcc atttccatgt ggaagagttt   1560
ctgtttcaca aacttctaag ctcacccgtg ctgagactgt tttcctgat gtggactatg   1620
taaattctac tgaagctgaa accattttgg ataacatcac tcaaagcacc caatcattta   1680
atgacttcac tcgggttgtt ggtggagaag atgccaaacc aggtcaattc ccttggcagg   1740
ttgttttgaa tggtaaagtt gatgcattct gtggaggctc tatcgttaat gaaaaatgga   1800
ttgtaactgc tgcccactgt gttgaaactg gtgttaaaat tacagttgtc gcaggtgaac   1860
ataatattga ggagacagaa catacagagc aaaagcgaaa tgtgattcga attattcctc   1920
accacaacta caatgcagct attaataagt acaaccatga cattgccctt ctggaactgg   1980
acgaaccctt agtgctaaac agctacgtta cacctatttg cattgctgac aaggaataca   2040
cgaacatctt cctcaaattt ggatctggct atgtaagtgg ctggggaagg gtcttccaca   2100
aagggagatc agctttagtt cttcagtacc ttagagttcc acttgttgac cgagccacat   2160
gtcttcgatc tacaaagttc accatctata acaacatgtt ctgtgctggc ttccatgaag   2220
gaggtagaga ttcatgtcaa ggagatagtg gggaccccca tgttactgaa gtggaaggga   2280
ccagtttctt aactggaatt attagctggg gtgaagagtg tgcaatgaaa ggcaaatatg   2340
gaatatatac caaggtatcc cggtatgtca actggattaa ggaaaaaaca aagctcactt   2400
aatgaaagat ggatttccaa ggatccagca cagtggcggc cgctcggttc ctagagggcc   2460
cgtttaaacc cgctgatcag cctcgactgt gccttctagt tgccagccat ctgttgtttg   2520
cccctccccc gtgccttcct tgaccctgga aggtgccact cccactgtcc tttcctaata   2580
aaatgaggaa attgcatcgc attgtctgag taggtgtcat tctattctgg ggggtggggt   2640
ggggcaggac agcaaggggg aggattggga agacaatagc aggcatgctg gggatgcggt   2700
gggctctatg gcttctgagg cggaaagaac cagctggggc tctagggggt atccccacgc   2760
gccctgtagc ggcgcattaa gcgcggcggg tgtggtggtt acgcgcagcg tgaccgctac   2820
acttgccagc gccctagcgc ccgctccttt cgctttcttc ccttcctttc tcgccacgtt   2880
```

-continued

```
cgccggcttt ccccgtcaag ctctaaatcg gggggctccct ttagggttcc gatttagtgc   2940
tttacggcac ctcgacccca aaaaacttga ttagggtgat ggttcacatc gatgcaattt   3000
cctcatttta ttaggaaagg acagtgggag tggcaccttc cagggtcaag gaaggcacgg   3060
gggaggggca aacaacagat ggctggcaac tagaaggcac agtcgaggct gatcagcggg   3120
tttaaacggg ccctctagac tcgaattgcc cttccaacat ctggccccct tcagaactct   3180
gagtggacag gatcaggatt tgactcagga ggattagaat gtgaagaatc cgtgtttgag   3240
ggattcagtt ctccaactgc ctcaaagggt ctcaagtttg cataagtcac ctcctgggcc   3300
agctgctcca gggaaggacg gcctaatatc agatttcgaa gtgagataca agtcatcagg   3360
aagctgcggc gaaagacata gagctttcgc aacaagaagc ggaagaatcg ctcatggaaa   3420
ggagtatttc gccggcgttc aatctcctgg agcctttgtt ggcgtctaag aaaggtctga   3480
accagaggtg ttggctcagg gcccccttttt acttcccctt ccaacagagg ctgcagctct   3540
gggggtagag gccctgtttc acttccattc tccacctttt cctttaattc ttgcagatat   3600
gccaggtctt gctccagtgc aagctctgta gtgttgacat agacgtacat gtagcaagaa   3660
gggctaggtg atgtcgtata caccttatgg tactcaccag caggcaactg cattttttct   3720
ccctctcgaa gagtctggtt cttctgttct gccacaagct ccacagtcac ttccccctgc   3780
agcagctgga tgctagtgtt gcccaggtct tcactcacaa aattctccaa gtgcagtcca   3840
gggaaatctg caatgaagac cacctcagtg tggttgtcta ggctgctctt gatttcctgt   3900
aacttggccc tccagggaga caggtccatc aagagtggtt gcacccagga tgtgcgctga   3960
aagggtgacc aagcggcctg cacgatgtcc acacgagggt caaaaatcct ctgctggaag   4020
cggtcattga tggagaccca aatatcaaag tagatctggg gctcagtgac attatacttg   4080
ggaagcaggc ggctcaggca agtggcatat tgcttcagca tgtctgcatg atccttccat   4140
cgccgactct gtgtaaatac cccagggtta aggtagccca gttcgccagt gcggccatca   4200
cggtaggtga tcttcacgtg ctggtgggag cgggagtgca ccatcatgtc ccaggaatag   4260
ccatacagcc catttgtcca gttgttatag ccctgggtga gaaaatgaga atagggcagg   4320
aatagctgct ccaggaggta gagcagggtg aaggcagctc ccagctgatg gcgcagccct   4380
ggcttctggc cacttttgcc ccggctcctc ttatacacac aggaaacact gggctgaggg   4440
gctgccttga ggggcaacag ttgttgcaac cttcgggggc agtaggacac cagcttccga   4500
ggccactcag gggagcagaa gagagggctg ctggccagca tgacgtagga gaacatacca   4560
atgctgaaaa gctgggaatt catgcagtgg aagtaggaca caaagaacag gccaatggat   4620
cttgagacat caaaaaagag caggaaacca gctgagaggt caagcagcag cccaccccag   4680
tgcacgacca gcaggctagt cagctcctca gacaacagca gtttgaaggg actgaagagc   4740
cagtgccggg acaaatattc catggaatag ccttcaaccc agtctgcatc cagctttttc   4800
acacccgcaa tgaagtacac aatgaagatc tggccacgga gcactgcata gttccaaagg   4860
ggcacgtggg cattcctcct atgggcattc agcagaccgt ccacagacca gtagtggttt   4920
gcatccatga atgttagctg aaaggccaac aacccataca gataggagtg gttgttccat   4980
gatgtcttgt ccaggagaaa cacataccag tatggcagca ggaataacac acagcttatc   5040
cggtagcaca ggcccagcat catgcccagt gcccccagaa acatgatggt gtagacaaga   5100
tacatccagt caagtggcag tgggcgtagg gcatccagca aggggaagcg gcacacatcc   5160
agcccatcaa ggtatttccg gtccagagag ctgagccccc gctcctgggg aatgtctagc   5220
```

-continued

```
accatcaaga acccaaaaag aaaacgaaag acagctaagc ttgcagggtc cgttggtcga   5280
ttcagcaggg tcaccagcct ccgccaactg gacaaatctg tccactcaaa acccaagagt   5340
ttccctattc ggctgtcctg cctgggccct gagatcagtt cagccttgtc tttctgtact   5400
ttatctgagc tgggcgaggt ccgcgcggac ccggcagaca ccgccattgc tctgcggaaa   5460
gggcaattcc accacactgg actagtggat ccgagctcgg taccaagctt aagtttaaac   5520
gctagccagc ttgggtctcc ctatagtgag tcgtattaat ttcgataagc cagtaagcag   5580
tgggttctct agttagccag agagcttttt gcaaaagcct aggcctccaa aaaagcctcc   5640
tcactacttc tggaatagct cagaggccga ggcggcctcg gcctctgcat aaataaaaaa   5700
aattagtcag ccatggggcg gagaatgggc ggaactgggc ggagttaggg gcgggatggg   5760
cggagttagg ggcgggacta tggttgctga ctaattgaga tgcatgcttt gcatacttct   5820
gcctgctggg gagcctgggg actttccaca ccctaactga cacacattcc acagccggat   5880
cgatgtgggc catcgccctg atagacggtt tttcgccctt tgacgttgga gtccacgttc   5940
tttaatagtg gactcttgtt ccaaactgga acaacactca accctatctc ggtctattct   6000
tttgatttat aagggatttt gccgatttcg gcctattggt taaaaaatga gctgatttaa   6060
caaaaattta acgcgaatta attctgtgga atgtgtgtca gttagggtgt ggaaagtccc   6120
caggctcccc agcaggcaga agtatgcaaa gcatgcatct caattagtca gcaaccaggt   6180
gtggaaagtc cccaggctcc ccagcaggca gaagtatgca aagcatgcat ctcaattagt   6240
cagcaaccat agtcccgccc ctaactccgc ccatcccgcc cctaactccg cccagttccg   6300
cccattctcc gccccatggc tgactaattt tttttattta tgcagaggcc gaggccgcct   6360
ctgcctctga gctattccag aagtagtgag gaggcttttt tggaggccta ggcttttgca   6420
aaaagctccc gggagcttgt atatccattt tcggatctga tcaagagaca ggatgaggat   6480
cgtttcgcat gattgaacaa gatggattgc acgcaggttc tccggccgct tgggtggaga   6540
ggctattcgg ctatgactgg gcacaacaga caatcggctg ctctgatgcc gccgtgttcc   6600
ggctgtcagc gcaggggcgc ccggttcttt ttgtcaagac cgacctgtcc ggtgccctga   6660
atgaactgca ggacgaggca gcgcggctat cgtggctggc cacgacgggc gttccttgcg   6720
cagctgtgct cgacgttgtc actgaagcgg gaagggactg gctgctattg ggcgaagtgc   6780
cggggcagga tctcctgtca tctcaccttg ctcctgccga gaaagtatcc atcatggctg   6840
atgcaatgcg gcggctgcat acgcttgatc cggctacctg cccattcgac caccaagcga   6900
aacatcgcat cgagcgagca cgtactcgga tggaagccgg tcttgtcgat caggatgatc   6960
tggacgaaga gcatcagggg ctcgcgccag ccgaactgtt cgccaggctc aaggcgcgca   7020
tgcccgacgg cgaggatctc gtcgtgaccc atggcgatgc ctgcttgccg aatatcatgg   7080
tggaaaatgg ccgcttttct ggattcatcg actgtggccg gctgggtgtg gcggaccgct   7140
atcaggacat agcgttggct acccgtgata ttgctgaaga gcttggcggc gaatgggctg   7200
accgcttcct cgtgctttac ggtatcgccg ctcccgattc gcagcgcatc gccttctatc   7260
gccttcttga cgagttcttc tgagcgggac tctggggttc gaaatgaccg accaagcgac   7320
gcccaacctg ccatcacgag atttcgattc caccgccgcc ttctatgaaa ggttgggctt   7380
cggaatcgtt ttccgggacg ccggctggat gatcctccag cgcggggatc tcatgctgga   7440
gttcttcgcc caccccaact tgtttattgc agcttataat ggttacaaat aaagcaatag   7500
catcacaaat ttcacaaata aagcattttt ttcactgcat tctagttgtg gtttgtccaa   7560
actcatcaat gtatcttatc atgtctgtat accgtcgacc tctagctaga gcttggcgta   7620
```

-continued

```
atcatggtca tagctgtttc ctgtgtgaaa ttgttatccg ctcacaattc cacacaacat   7680
acgagccgga agcataaagt gtaaagcctg gggtgcctaa tgagtgagct aactcacatt   7740
aattgcgttg cgctcactgc ccgctttcca gtcgggaaac ctgtcgtgcc agctgcatta   7800
atgaatcggc caacgcgcgg ggagaggcgg tttgcgtatt gggcgctctt ccgcttcctc   7860
gctcactgac tcgctgcgct cggtcgttcg gctgcggcga gcggtatcag ctcactcaaa   7920
ggcggtaata cggttatcca cagaatcagg ggataacgca ggaaagaaca tgtgagcaaa   7980
aggccagcaa aaggccagga accgtaaaaa ggccgcgttg ctggcgtttt tccataggct   8040
ccgcccccct gacgagcatc acaaaaatcg acgctcaagt cagaggtggc gaaacccgac   8100
aggactataa agataccagg cgtttccccc tggaagctcc ctcgtgcgct ctcctgttcc   8160
gaccctgccg cttaccggat acctgtccgc ctttctccct tcgggaagcg tggcgctttc   8220
tcatagctca cgctgtaggt atctcagttc ggtgtaggtc gttcgctcca agctgggctg   8280
tgtgcacgaa ccccccgttc agcccgaccg ctgcgcctta tccggtaact atcgtcttga   8340
gtccaacccg gtaagacacg acttatcgcc actggcagca gccactggta acaggattag   8400
cagagcgagg tatgtaggcg gtgctacaga gttcttgaag tggtggccta actacggcta   8460
cactagaaga acagtatttg gtatctgcgc tctgctgaag ccagttacct tcggaaaaag   8520
agttggtagc tcttgatccg gcaaacaaac caccgctggt agcggttttt ttgtttgcaa   8580
gcagcagatt acgcgcagaa aaaaaggatc tcaagaagat cctttgatct tttctacggg   8640
gtctgacgct cagtggaacg aaaactcacg ttaagggatt ttggtcatga gattatcaaa   8700
aaggatcttc acctagatcc ttttaaatta aaaatgaagt tttaaatcaa tctaaagtat   8760
atatgagtaa acttggtctg acagttacca atgcttaatc agtgaggcac ctatctcagc   8820
gatctgtcta tttcgttcat ccatagttgc ctgactcccc gtcgtgtaga taactacgat   8880
acgggagggc ttaccatctg gccccagtgc tgcaatgata ccgcgagacc cacgctcacc   8940
ggctccagat ttatcagcaa taaaccagcc agccggaagg gccgagcgca gaagtggtcc   9000
tgcaacttta tccgcctcca tccagtctat taattgttgc cgggaagcta gagtaagtag   9060
ttcgccagtt aatagtttgc gcaacgttgt tgccattgct acaggcatcg tggtgtcacg   9120
ctcgtcgttt ggtatggctt cattcagctc cggttcccaa cgatcaaggc gagttacatg   9180
atcccccatg ttgtgcaaaa aagcggttag ctccttcggt cctccgatcg ttgtcagaag   9240
taagttggcc gcagtgttat cactcatggt tatggcagca ctgcataatt ctcttactgt   9300
catgccatcc gtaagatgct tttctgtgac tggtgagtac tcaaccaagt cattctgaga   9360
atagtgtatg cggcgaccga gttgctcttg cccggcgtca atacgggata ataccgcgcc   9420
acatagcaga actttaaaag tgctcatcat tggaaaacgt tcttcggggc gaaaactctc   9480
aaggatctta ccgctgttga gatccagttc gatgtaaccc actcgtgcac ccaactgatc   9540
ttcagcatct tttactttca ccagcgtttc tgggtgagca aaaacaggaa ggcaaaatgc   9600
cgcaaaaaag ggaataaggg cgacacggaa atgttgaata ctcatactct tcctttttca   9660
atattattga agcatttatc agggttattg tctcatgagc ggatacatat ttgaatgtat   9720
ttagaaaaat aaacaaatag gggttccgcg cacatttccc cgaaaagtgc cacctgacgt   9780
c                                                                   9781
```